(12) United States Patent
McIninch

(10) Patent No.: US 7,444,243 B2
(45) Date of Patent: Oct. 28, 2008

(54) PROBABILISTIC METHOD FOR DETERMINING NUCLEIC ACID CODING FEATURES

(75) Inventor: James D. McIninch, Burlington, MA (US)

(73) Assignee: Monsanto Technology LLC, St. Louis, MO (US)

( * ) Notice: Subject to any disclaimer, the term of this patent is extended or adjusted under 35 U.S.C. 154(b) by 223 days.

(21) Appl. No.: 10/775,176

(22) Filed: Feb. 11, 2004

(65) Prior Publication Data

US 2004/0203041 A1   Oct. 14, 2004

Related U.S. Application Data

(63) Continuation of application No. 09/698,213, filed on Oct. 30, 2000, now abandoned.

(51) Int. Cl.
G06F 19/00 (2006.01)
(52) U.S. Cl. ............................. 702/19; 702/20; 703/2; 703/11
(58) Field of Classification Search ........................ None
See application file for complete search history.

(56) References Cited

U.S. PATENT DOCUMENTS

2002/0183934 A1*  12/2002  Selifonov et al. ............. 702/19

OTHER PUBLICATIONS

Borodovsky et al., "Genmark: Parallel gene recognition for both DNA strands", 1993, Computers & Chemistry, vol. 17, Issue 2, pp. 123-133.*

* cited by examiner

*Primary Examiner*—Carolyn L. Smith
(74) *Attorney, Agent, or Firm*—David J. Chi; Maria Margarita D. Unson; Thomas E. Kelley

(57) ABSTRACT

The present invention is in the field of bioinformatics, particularly as it pertains to gene prediction. More specifically, the invention relates to the probabilistic analysis of nucleic acid sequences for the determination of coding features, including determination of state probabilities for each nucleotide in a nucleic acid sequence, determination of coding strand, determination of open reading frame extent, determination of insertion and deletion location, determination of exon location, and determination of protein sequence.

4 Claims, 11 Drawing Sheets

SEQUENCE LISTING

<160> NUMBER OF SEQ ID NOS: 4

<210> SEQ ID NO 1
<211> LENGTH: 2165
<212> TYPE: DNA
<213> ORGANISM: Arabidopsis thaliana
<220> FEATURE:
<221> NAME/KEY: modified_base
<222> LOCATION: (2042)
<223> OTHER INFORMATION: a, c, g, t, unknown or other
<220> FEATURE:
<221> NAME/KEY: modified_base
<222> LOCATION: (2061)
<223> OTHER INFORMATION: a, c, g, t, unknown or other

<400> SEQUENCE: 1

```
tactcaaaaa tatattccat gcttaattag gccggattcg cggtgacgat gcaccaagag      60 cggttttcc  gagcattgta ggccgtcctc gccacaccgg tgtgatggtt gggatgggac     120
aaaaggatgc ttatgttgga gacgaggctc aatcaaaacg tggtatcttg actctgaagt    180
acccaattga gcatggaatt gttaataatt gggatgacat ggagaagatt tggcatcaca    240
ctttctacaa tgagcttcgt gttgcccctg aagaacatcc ggttctcttg accgaagctc    300
ctctcaatcc gaaagctaac cgtgagaaga tgactcagat catgtttgag acattcaata    360
ctcctgctat gtatgttgcc attcaagctg ttctctcact ctatgccagt ggccgtacta    420
ctggtcagta cattactaca ttcttttttat accgtttggt tgaaataaaa ttcggtttgg    480
ttcgattcga gtttgctctc attattttta ttttgttggt taggtattgt tttggactcc    540
ggagatggtg tgagccacac ggtaccaatc tacgagggtt atgcacttcc acacgcaatc    600
ctgcgtcttg atcttgcagg tcgtgaccta accgaccacc ttatgaaaat cctgacagag    660
cgtggttact ctttcaccac aactgctgag cgtgagattg ttagagacat gaaggagaag    720
ctctcttaca ttgccttgga ctttgaacaa gagctcgaga cttccaaaac aagctcatcc    780
gttgagaaga gcttcgagct gccagacggt caagtgatca ccatcggggc agagcgtttc    840
cgatgccctg aagttctgtt tcagccatcg atgatcggaa tggaaaatcc gggaattcat    900
gaaactactt acaactcaat catgaaatgt gatgtggata tcaggaagga tctttatgga    960
aacattgtgc ttagtggtgg caccacaatg ttcgatggga ttggtgatag gatgagtaaa   1020
gagatcacag cgttggctcc aagcagtatg aacatcaaag tggtggctcc accggaaagg   1080
aagtacagtg tctggatcgg tggctctatc ttggcttccc tcagtacttt ccagcaggta   1140
aattacttac tatacttaat acataaagtc tattagtgat ttgatgtata agtgttaca    1200 aaaatgtgtt ccaaatttgc agatgtggat tgcgaaagcg gagtatgatg aatctggacc   1260
gtcaatcgtc cacaggaagt gcttctgatc aaaagtcacc aagtaaaaca agagcggtaa   1320
```

```
aaatttttgat  atcagttttt  caccctgaag  ccagttgcta  taattactca  caacttctct    1380
atttgtgttc  ttttattctt  gtccctcgtt  gttcatttta  atctctttt   tgcaacaaag    1440 caacttaaaa  aaacagagca  gtcattaaca  gaatgttatt  attatatata  tgtatacata    1500
ttagtataca  cccattattt  cattaaaaca  tttatcatat  aaggatagga  ttctatacat    1560
cgatatattt  attttgttga  cactattcag  cacatgctta  tgtcttatct  tgttagtata    1620
tgtaaccaaa  gacaaataat  agatgctaca  aattgttttc  tttgaagcaa  aaatttcaat    1680
cttaaaattg  ttttttttcca  ggttacacaa  aaaaaacttg  tagtttgtaa  attttctata   1740
caattttggg  gatctcaaca  agaacatgaa  cttcaacttc  tagtcatatg  acgacctgag    1800
tctgcgcggc  tgtgaatctc  tttgctgcag  taaatgttta  caagtggtgt  gtaaattggt    1860
actgattcaa  aagctttaag  aaatctacac  atttcgtgaa  attatttagc  agacttgata    1920
ttaaaaatct  aggataaaat  gactatccaa  agacaaatag  gactgtttca  catgttcccc    1980
tgattcttgt  agctcataac  tcatcagcag  ttaacttttc  tacctcatac  acgctcgcaa    2040
tncgtttgga  attatcagct  ntaatttttc  taattctttg  gaaattatta  gcagctcgat    2100
caaatggggc  atggcttctt  cttctatctg  caactcatct  aaactttcca  tgaagaaaca    2160
aagct                                                                      2165
```

<210> SEQ ID NO 2
<211> LENGTH: 412
<212> TYPE: PRT
<213> ORGANISM: Artificial Sequence
<220> FEATURE:
<223> OTHER INFORMATION: Description of Artificial Sequence: Predicted
      synthetic amino acid sequence
<220> FEATURE:
<221> NAME/KEY: SITE
<222> LOCATION: (1)
<223> OTHER INFORMATION: There is a predicted stop codon present before
      the codon in corresponding SEQ ID NO: 1 that codes for residue 1
      of the instant sequence.
<220> FEATURE:
<221> NAME/KEY: SITE
<222> LOCATION: (6)..(7)
<223> OTHER INFORMATION: There is a predicted stop codon present between
      the codons in corresponding SEQ ID NO: 1 that code
      for residues 6 to 7 of the instant sequence.
<220> FEATURE:
<221> NAME/KEY: SITE
<222> LOCATION: (13)..(14)
<223> OTHER INFORMATION: There is a predicted stop codon present between
      the codons in corresponding SEQ ID NO: 1 that code
      for residues 13 to 14 of the instant sequence.
<220> FEATURE:
<221> NAME/KEY: SITE
<222> LOCATION: (34)..(35)
<223> OTHER INFORMATION: There is a predicted stop codon present between
      the codons in corresponding SEQ ID NO: 1 that code
      for residues 34 to 35 of the instant sequence.
<220> FEATURE:
<221> NAME/KEY: SITE
<222> LOCATION: (35)..(36)
<223> OTHER INFORMATION: There is a predicted stop codon present between
      the codons in corresponding SEQ ID NO: 1 that code
      for residues 35 to 36 of the instant sequence.
<220> FEATURE:
<221> NAME/KEY: SITE
<222> LOCATION: (70)..(71)
<223> OTHER INFORMATION: There is a predicted stop codon present between
      the codons in corresponding SEQ ID NO: 1 that code
      for residues 70 to 71 of the instant sequence.
<220> FEATURE:
<221> NAME/KEY: SITE
<222> LOCATION: (126)..(127)
<223> OTHER INFORMATION: There is a predicted stop codon present between
      the codons in corresponding SEQ ID NO: 1 that code

```
        for residues 126 to 127 of the instant sequence.
<220> FEATURE:
<221> NAME/KEY: SITE
<222> LOCATION: (317)..(318)
<223> OTHER INFORMATION: There is a predicted stop codon present between
      the codons in corresponding SEQ ID NO: 1 that code
      for residues 317 to 318 of the instant sequence.
<220> FEATURE:
<221> NAME/KEY: SITE
<222> LOCATION: (330)..(331)
<223> OTHER INFORMATION: There is a predicted stop codon present between
      the codons in corresponding SEQ ID NO: 1 that code
      for residues 330 to 331 of the instant sequence.
<220> FEATURE:
<221> NAME/KEY: SITE
<222> LOCATION: (356)..(357)
<223> OTHER INFORMATION: There is a predicted stop codon present between
      the codons in corresponding SEQ ID NO: 1 that code
      for residues 356 to 357 of the instant sequence.
<220> FEATURE:
<221> NAME/KEY: SITE
<222> LOCATION: (412)
<223> OTHER INFORMATION: There is a predicted stop codon present after
      the codon in corresponding SEQ ID NO: 1 that codes for residue 412
      of the instant sequence.

<400> SEQUENCE: 2

Arg Phe Phe Arg Ala Leu Ala Val Leu Ala Thr Pro Val Trp Leu Gly
 1               5                  10                  15

Trp Asp Lys Arg Met Leu Met Leu Glu Thr Arg Leu Asn Gln Asn Val
            20                  25                  30

Val Ser Leu Ser Thr Gln Leu Ser Met Glu Leu Leu Ile Ile Gly Met
        35                  40                  45

Thr Trp Arg Arg Phe Gly Ile Thr Leu Ser Thr Met Ser Phe Val Leu
    50                  55                  60

Pro Leu Lys Asn Ile Arg Leu Thr Glu Ala Pro Leu Asn Pro Lys Ala
65                  70                  75                  80

Asn Arg Glu Lys Met Thr Gln Ile Met Phe Glu Thr Phe Asn Thr Pro
                85                  90                  95

Ala Met Tyr Val Ala Ile Gln Ala Val Leu Ser Leu Tyr Ala Ser Gly
            100                 105                 110

Arg Thr Thr Gly Gln Tyr Ile Thr Thr Phe Phe Leu Tyr Arg Ser Gly
        115                 120                 125

Asp Gly Val Ser His Thr Val Pro Ile Tyr Glu Gly Tyr Ala Leu Pro
    130                 135                 140

His Ala Ile Leu Arg Leu Asp Leu Ala Gly Arg Asp Leu Thr Asp His
145                 150                 155                 160

Leu Met Lys Ile Leu Thr Glu Arg Gly Tyr Ser Phe Thr Thr Thr Ala
                165                 170                 175

Glu Arg Glu Ile Val Arg Asp Met Lys Glu Lys Leu Ser Tyr Ile Ala
            180                 185                 190

Leu Asp Phe Glu Gln Glu Leu Glu Thr Ser Lys Thr Ser Ser Ser Val
        195                 200                 205

Glu Lys Ser Phe Glu Leu Pro Asp Gly Gln Val Ile Thr Ile Gly Ala
    210                 215                 220

Glu Arg Phe Arg Cys Pro Glu Val Leu Phe Gln Pro Ser Met Ile Gly
225                 230                 235                 240

Met Glu Asn Pro Gly Ile His Glu Thr Thr Tyr Asn Ser Ile Met Lys
                245                 250                 255

Cys Asp Val Asp Ile Arg Lys Asp Leu Tyr Gly Asn Ile Val Leu Ser
            260                 265                 270
```

```
Gly Gly Thr Thr Met Phe Asp Gly Ile Gly Asp Arg Met Ser Lys Glu
            275                 280                 285

Ile Thr Ala Leu Ala Pro Ser Ser Met Lys Ile Lys Val Val Ala Pro
            290                 295                 300

Pro Glu Arg Lys Tyr Ser Val Trp Ile Gly Gly Ser Ile Val Pro Asn
305                 310                 315                 320

Leu Gln Met Trp Ile Ala Lys Ala Glu Tyr Asn Leu Asp Arg Gln Ser
                325                 330                 335

Ser Thr Gly Ser Ala Ser Asp Gln Lys Ser Pro Ser Lys Thr Arg Ala
            340                 345                 350

Val Lys Ile Leu Asn Ser Ser Ala Val Asn Phe Ser Thr Ser Tyr Thr
            355                 360                 365

Leu Ala Ile Arg Leu Glu Leu Ser Ala Leu Ile Phe Leu Ile Ser Leu
            370                 375                 380

Glu Ile Ile Ser Ser Ile Lys Trp Gly Met Ala Ser Ser Ser Ile
385                 390                 395                 400

Cys Asn Ser Ser Lys Leu Ser Met Lys Lys Gln Ser
            405                 410
```

<210> SEQ ID NO 3
<211> LENGTH: 411
<212> TYPE: PRT
<213> ORGANISM: Artificial Sequence
<220> FEATURE:
<223> OTHER INFORMATION: Description of Artificial Sequence: Predicted
      synthetic amino acid sequence
<220> FEATURE:
<221> NAME/KEY: SITE
<222> LOCATION: (1)
<223> OTHER INFORMATION: There is a predicted stop codon present before
      the codon in corresponding SEQ ID NO: 1 that codes for residue 1
      of the instant sequence.
<220> FEATURE:
<221> NAME/KEY: SITE
<222> LOCATION: (6)..(7)
<223> OTHER INFORMATION: There is a predicted stop codon present between
      the codons in corresponding SEQ ID NO: 1 that code
      for residues 6 to 7 of the instant sequence.
<220> FEATURE:
<221> NAME/KEY: SITE
<222> LOCATION: (13)..(14)
<223> OTHER INFORMATION: There is a predicted stop codon present between
      the codons in corresponding SEQ ID NO: 1 that code
      for residues 13 to 14 of the instant sequence.
<220> FEATURE:
<221> NAME/KEY: SITE
<222> LOCATION: (34)..(35)
<223> OTHER INFORMATION: There is a predicted stop codon present between
      the codons in corresponding SEQ ID NO: 1 that code
      for residues 34 to 35 of the instant sequence.
<220> FEATURE:
<221> NAME/KEY: SITE
<222> LOCATION: (35)..(36)
<223> OTHER INFORMATION: There is a predicted stop codon present between
      the codons in corresponding SEQ ID NO: 1 that code
      for residues 35 to 36 of the instant sequence.
<220> FEATURE:
<221> NAME/KEY: SITE
<222> LOCATION: (70)..(71)
<223> OTHER INFORMATION: There is a predicted stop codon present between
      the codons in corresponding SEQ ID NO: 1 that code
      for residues 70 to 71 of the instant sequence.
<220> FEATURE:
<221> NAME/KEY: SITE
<222> LOCATION: (126)..(127)
<223> OTHER INFORMATION: There is a predicted stop codon present between
      the codons in corresponding SEQ ID NO: 1 that code
      for residues 126 to 127 of the instant sequence.
<220> FEATURE:
<221> NAME/KEY: SITE

```
<222> LOCATION: (320)..(321)
<223> OTHER INFORMATION: There is a predicted stop codon present between
      the codons in corresponding SEQ ID NO: 1 that code
      for residues 320 to 321 of the instant sequence.
<220> FEATURE:
<221> NAME/KEY: SITE
<222> LOCATION: (329)..(330)
<223> OTHER INFORMATION: There is a predicted stop codon present between
      the codons in corresponding SEQ ID NO: 1 that code
      for residues 329 to 330 of the instant sequence.
<220> FEATURE:
<221> NAME/KEY: SITE
<222> LOCATION: (355)..(356)
<223> OTHER INFORMATION: There is a predicted stop codon present between
      the codons in corresponding SEQ ID NO: 1 that code
      for residues 355 to 356 of the instant sequence.
<220> FEATURE:
<221> NAME/KEY: SITE
<222> LOCATION: (411)
<223> OTHER INFORMATION: There is a predicted stop codon present after
      the codon in corresponding SEQ ID NO: 1 that codes for the residue
      411 of the instant sequence.

<400> SEQUENCE: 3

Arg Phe Phe Arg Ala Leu Ala Val Leu Ala Thr Pro Val Trp Leu Gly
 1               5                  10                  15

Trp Asp Lys Arg Met Leu Met Leu Glu Thr Arg Leu Asn Gln Asn Val
            20                  25                  30

Val Ser Leu Ser Thr Gln Leu Ser Met Glu Leu Leu Ile Ile Gly Met
        35                  40                  45

Thr Trp Arg Arg Phe Gly Ile Thr Leu Ser Thr Met Ser Phe Val Leu
    50                  55                  60

Pro Leu Lys Asn Ile Arg Leu Thr Glu Ala Pro Leu Asn Pro Lys Ala
65                  70                  75                  80

Asn Arg Glu Lys Met Thr Gln Ile Met Phe Glu Thr Phe Asn Thr Pro
                85                  90                  95

Ala Met Tyr Val Ala Ile Gln Ala Val Leu Ser Leu Tyr Ala Ser Gly
            100                 105                 110

Arg Thr Thr Gly Gln Tyr Ile Thr Thr Phe Phe Leu Tyr Arg Ser Gly
        115                 120                 125

Asp Gly Val Ser His Thr Val Pro Ile Tyr Glu Gly Tyr Ala Leu Pro
130                 135                 140

His Ala Ile Leu Arg Leu Asp Leu Ala Gly Arg Asp Leu Thr Asp His
145                 150                 155                 160

Leu Met Lys Ile Leu Thr Glu Arg Gly Tyr Ser Phe Thr Thr Thr Ala
                165                 170                 175

Glu Arg Glu Ile Val Arg Asp Met Lys Glu Lys Leu Ser Tyr Ile Ala
            180                 185                 190

Leu Asp Phe Glu Gln Glu Leu Glu Thr Ser Lys Thr Ser Ser Ser Val
        195                 200                 205

Glu Lys Ser Phe Glu Leu Pro Asp Gly Gln Val Ile Thr Ile Gly Ala
    210                 215                 220

Glu Arg Phe Arg Cys Pro Glu Val Leu Phe Gln Pro Ser Met Ile Gly
225                 230                 235                 240

Met Glu Asn Pro Gly Ile His Glu Thr Thr Tyr Asn Ser Ile Met Lys
                245                 250                 255

Cys Asp Val Asp Ile Arg Lys Asp Leu Tyr Gly Asn Ile Val Leu Ser
            260                 265                 270

Gly Gly Thr Thr Met Phe Asp Gly Ile Gly Asp Arg Met Ser Lys Glu
        275                 280                 285
```

```
Ile Thr Ala Leu Ala Pro Ser Ser Met Lys Ile Lys Val Val Ala Pro
    290                 295                 300

Pro Glu Arg Lys Tyr Ser Val Trp Ile Gly Gly Ser Ile Leu Ala Ser
305                 310                 315                 320

Gln Met Trp Ile Ala Lys Ala Glu Tyr Asn Leu Asp Arg Gln Ser Ser
                325                 330                 335

Thr Gly Ser Ala Ser Asp Gln Lys Ser Pro Ser Lys Thr Arg Ala Val
            340                 345                 350

Lys Ile Leu Asn Ser Ser Ala Val Asn Phe Ser Thr Ser Tyr Thr Leu
        355                 360                 365

Ala Ile Arg Leu Glu Leu Ser Ala Leu Ile Phe Leu Ile Ser Leu Glu
    370                 375                 380

Ile Ile Ser Ser Ser Ile Lys Trp Gly Met Ala Ser Ser Ser Ile Cys
385                 390                 395                 400

Asn Ser Ser Lys Leu Ser Met Lys Lys Gln Ser
                405                 410

<210> SEQ ID NO 4
<211> LENGTH: 355
<212> TYPE: PRT
<213> ORGANISM: Arabidopsis thaliana

<400> SEQUENCE: 4

Gly Asp Asp Ala Pro Arg Ala Val Phe Pro Ser Ile Val Gly Arg Pro
1               5                   10                  15

Arg His Thr Gly Val Met Val Gly Met Gly Gln Lys Asp Ala Tyr Val
            20                  25                  30

Gly Asp Glu Ala Gln Ser Lys Arg Gly Ile Leu Thr Leu Lys Tyr Pro
        35                  40                  45

Ile Glu His Gly Ile Val Asn Asn Trp Asp Asp Met Glu Lys Ile Trp
    50                  55                  60

His His Thr Phe Tyr Asn Glu Leu Arg Val Ala Pro Glu Glu His Pro
65                  70                  75                  80

Val Leu Leu Thr Glu Ala Pro Leu Asn Pro Lys Ala Asn Arg Glu Lys
                85                  90                  95

Met Thr Gln Ile Met Phe Glu Thr Phe Asn Thr Pro Ala Met Tyr Val
            100                 105                 110

Ala Ile Gln Ala Val Leu Ser Leu Ala Ser Gly Arg Thr Thr Gly Gly
        115                 120                 125

Ile Val Leu Asp Ser Gly Asp Gly Val Ser His Thr Val Pro Ile Tyr
    130                 135                 140

Glu Gly Tyr Ala Leu Pro His Ala Ile Leu Arg Leu Asp Leu Ala Gly
145                 150                 155                 160

Arg Asp Leu Thr Asp His Leu Met Lys Ile Leu Thr Glu Arg Gly Tyr
                165                 170                 175

Ser Phe Thr Thr Thr Ala Glu Arg Glu Ile Val Arg Asp Met Lys Glu
            180                 185                 190

Lys Leu Ser Tyr Ile Ala Leu Asp Phe Glu Gln Glu Leu Glu Thr Ser
        195                 200                 205

Lys Thr Ser Ser Ser Val Glu Lys Ser Phe Glu Leu Pro Asp Gly Gln
    210                 215                 220

Val Ile Thr Ile Gly Ala Glu Arg Phe Arg Cys Pro Glu Val Leu Phe
225                 230                 235                 240

Gln Pro Ser Met Ile Gly Met Glu Asn Pro Gly Ile His Glu Thr Thr
                245                 250                 255
```

```
Tyr Asn Ser Ile Met Lys Cys Asp Val Asp Ile Arg Lys Asp Leu Tyr
            260             265             270

Gly Asn Ile Val Leu Ser Gly Gly Thr Thr Met Phe Gly Gly Ile Gly
        275             280             285

Asp Arg Met Ser Lys Glu Ile Thr Ala Leu Ala Pro Ser Ser Met Lys
        290             295             300

Ile Lys Val Val Ala Pro Pro Glu Arg Lys Tyr Ser Val Trp Ile Gly
305             310             315             320

Gly Ser Ile Leu Ala Ser Leu Ser Thr Phe Gln Gln Met Gln Met Trp
                325             330             335

Ile Ala Lys Ala Glu Tyr Asp Glu Ser Gly Pro Ser Ile Val His Arg
            340             345             350

Lys Cys Phe
        355
```

PROBABILISTIC METHOD FOR DETERMINING NUCLEIC ACID CODING FEATURES

CROSS-REFERENCE TO RELATED APPLICATIONS

This application is a continuation of U.S. patent application Ser. No. 09/698,213, filed Oct. 30, 2000 now abandoned. U.S. patent application Ser. No. 09/698,213 is herein incorporated by reference in its entirety.

INCORPORATION OF SEQUENCE LISTING

A paper copy of the Sequence Listing and a computer readable form of the sequence listing on diskette, containing the file named 16517308.APP, which is 18,206 bytes in size (measured in MS-DOS), and which was created on Jun. 10, 2004, is herein incorporated by reference in its entirety.

FIELD OF THE INVENTION

The present invention is in the field of bioinformatics, particularly as it pertains to gene prediction. More specifically, the invention relates to the probabilistic analysis of nucleic acid sequences for the determination of coding features, including determination of state probabilities for each nucleotide in a nucleic acid sequence, determination of coding strand, determination of open reading frame extent, determination of insertion and deletion location, determination of exon location, and determination of protein sequence.

BACKGROUND OF THE INVENTION

Advances in techniques for sequencing long stretches of genomic deoxyribonucleic acid (DNA) have allowed investigators to collect vast nucleic acid sequence data rapidly. These advances, combined with initiatives to sequence the entire human genome and the genomes of several other species, have created a need for the rapid identification of genes on long stretches of sequenced DNA. Conventional gene location techniques, such as cDNA hybridization, are effective at locating transcribed genes, but are time-consuming and costly.

An alternative for locating genes on DNA that has not otherwise been analyzed for potential coding regions involves using statistical detection methods. Such methods conventionally include using probability models to predict where in a DNA sequence a gene is located. The theoretical nucleic acid sequence probabilities can be determined through analysis of known coding regions in the organism of interest. Once theoretical nucleic acid sequence probabilities are determined, nucleic acid sequences in unannotated regions of DNA in the same or a similar organism can be statistically compared to the theoretical nucleic acid sequence probabilities. If the similarity is sufficient, the investigator is notified that a coding sequence exists. Conventional cloning techniques can then be used to isolate the putative gene and check for transcription.

One type of statistical detection method searches DNA by content In such content-based models, highly conserved regions of DNA that are common to all genes are located. If a conserved region of DNA is found, then the nucleic acid sequence associated with the conserved region can be compared with known genes. Such comparisons, which can be done with nucleic acid sequence comparison programs such as BLAST, are inefficient to run, however, and content-based searches therefore have limited desirability.

A second type of statistical detection method searches DNA by signal. This type of searching involves using probability models to predict whether DNA fragments within a larger nucleic acid sequence are coding. Early searching by signal programs, such as TestCode and Grail, relied on statistical variations within coding regions of DNA, including codon frequency, local nucleic acid sequence composition, codon preference measures, heuristics based on oligonucleotide frequency variations, and measures of nucleic acid sequence complexity.

Beyond simple gene detection, there is also a need for the determination of other coding features, such as the location of intron/exon boundaries in eukaryotic organisms and the location of insertions or deletions. The program GENSCAN (Burge, C. and Karlin, S. (1997) Prediction of Complete Gene Structures in Human Genomic DNA. *J. Mol. Biol.* 268, 78-94), for example, predicts exon location with local state probabilities based on oligonucleotide usage. GENSCAN, however, also depends on non-local nucleic acid sequence characteristics, which make the program very sensitive to sequencing errors and genes containing alternative splicing strategies.

One statistical model that avoids the problems caused by dependence on non-local nucleic acid sequence characteristics is the inhomogeneous Markov model. An inhomogeneous Markov model depends upon local probabilities, and is not therefore sensitive to sequencing errors or genes with alternative splicing strategies. The inhomogeneous Markov model is "inhomogeneous" because it determines the state probabilities for a given nucleotide in multiple reading frames rather than in a single reading frame. GeneMark, for example, is a computer program that uses the inhomogeneous Markov model to locate genes.

The GeneMark gene prediction algorithm was developed in several steps. A series of three publications demonstrated that inhomogeneous Markov models were useful tools for gene prediction (see Borodovsky, M., Sprizhitsky Yu., Golovanov E. and Alexandrov A. (1986) Statistical Patterns in Primary Structures of Functional Regions in the E. Coli Genome: I. Oligonucleotide Frequencies Analysis, Molecular Biology, 20, 826-833, Borodovsky, M., Sprizhitsky Yu, Golovanov E. and Alexandrov A. (1986) Statistical Patterns in Primary Structures of Functional Regions in the E. Coli Genome: II. Non-homogeneous Markov Models, Molecular Biology, 20, 833-840, Borodovsky, M., Sprizhitsky Yu., Golovanov E. and Alexandrov A. (1986) Statistical Patterns in Primary Structures of Functional Regions in the E. Coli Genome: III. Computer Recognition of Coding Regions, Molecular Biology, 20, 1145-1150, all of which are herein incorporated by reference in their entirety). The GeneMark method was based on an inhomogeneous Markov model and was described in 1993 (see Borodovsky, M. and McIninch J. (1993) GeneMark, *Parallel Gene Recognition for both DNA Strands*, Computers & Chemistry, 17, 123-133, and Borodovsky, M. and McIninch J. (1993) BioSystems v30, pp. 161-171, both of which are herein incorporated by reference in their entirety). The capabilities of the GeneMark program were subsequently investigated (see James D. McIninch, *Prediction of Protein Coding Regions in Unannotated DNA sequences Using an Inhomogeneous Markov Model of Genetic Information Encoding* (1997) (Ph.D. dissertation, Georgia Institute of Technology, on file with the Georgia Institute of Technology Library, which is herein incorporated by reference in its entirety).

Conventional programs using inhomogeneous Markov models, however, are limited to a defined probabilistic model for determining probability, and cannot be tailored by the investigator to better suit the nucleic acid sequence under study if information about that nucleic acid sequence is already available. Further, conventional implementations do not allow for the efficient and accurate detection of other nucleic acid sequence features.

What is needed in the art is a method of determining state probabilities for a nucleic acid sequence having some known characteristics, where the method is insensitive to frameshift insertions or deletions, and compatible methods for detecting other nucleic acid sequence features in known or unknown nucleic acid sequences.

SUMMARY OF THE INVENTION

The present invention relates to the probabilistic analysis of nucleic acid sequences for the determination of coding features, including determination of state probabilities for each nucleotide in a nucleic acid sequence, determination of coding strand, determination of open reading frame extent, determination of insertion and deletion location, determination of exon location, and determination of protein sequence. Described herein are methods, devices, and systems for analyzing the information content in nucleic acids.

The present invention includes and provides a method for determining a probability for one or more states for a nucleotide in a nucleic acid sequence, comprising: a) determining an initial oligonucleotide probability for each of the states for an initial oligonucleotide in the nucleic acid sequence; b) determining transition probabilities for each of the states for nucleotides within the nucleic acid sequence following the initial oligonucleotide; c) determining a probability for the nucleic acid sequence for each of the states; and, d) determining a probability for each of the states for the nucleotide based upon the probability of the nucleic acid sequence and a bias.

The present invention includes and provides a method for determining a probability for one or more states for a nucleotide in a nucleic acid sequence, comprising: a) determining an initial oligonucleotide probability for each of the states for an initial oligonucleotide in the nucleic acid sequence; b) determining transition probabilities for each of the states for nucleotides within the nucleic acid sequence following the initial oligonucleotide; c) determining a probability for the nucleic acid sequence for each of the states; and, d) determining a probability for each of the states for the nucleotide based upon the probability of the nucleic acid sequence, wherein the determining a probability for each of the states is capable of accepting a bias.

The present invention includes and provides a method for determining a probability for each of one or more states for more than one nucleotide in a nucleic acid sequence comprising: a) determining an initial oligonucleotide probability for each of the states for an initial oligonucleotide in a window of a first nucleotide; b) determining transition probabilities for each of the states for nucleotides within the window following the initial oligonucleotide; c) determining a probability for the window for each of the states; d) determining a probability for each of the states for the nucleotide based upon the probability for the window and a bias; and, e) repeating steps a) through d) for each remaining nucleotide in the nucleic acid sequence.

The present invention includes and provides a method for determining strand coding of a nucleic acid sequence based upon a bias, comprising: a) determining a probability of each of one or more states for each nucleotide in the nucleic acid sequence, wherein each of the states is either a positive strand state or a negative strand state; b) summing the probabilities of the positive strand states for each of the nucleotides to produce a sum of probabilities for positive states; c) summing the probabilities of the negative strand states for each of the nucleotides to produce a sum of probabilities for negative states; and, d) deciding one of i) coding is mixed or not detectable if a first function of the sum of probabilities for positive states and the sum of probabilities for negative states is less than a threshold value; ii) coding is on the positive strand if a second function of the sum of probabilities for positive states is greater than a third function of the sum of probabilities for negative states and the first function is not less than the threshold value; and iii) coding is on the negative strand if the second function of the sum of probabilities for positive states is not greater than the third function of the sum of probabilities for negative states and the first function is not less than the threshold value.

The present invention includes and provides a method for determining the extent of an open reading frame within a nucleic acid sequence based upon a bias, comprising: a) determining the probability of each of one or more states for each nucleotide in the nucleic acid sequence, wherein each of the states is either a coding state or a noncoding state; b) determining the coding strand of the nucleic acid sequence; and, c) determining the points within the nucleic acid sequence in the coding strand at which the sum of the probabilities of the coding states for each nucleotide drops below a first threshold value for a number of nucleotides greater than a second threshold value, wherein ends of the open reading frame are indicated at the points.

The present invention includes and provides a method for determining the location of insertions and deletions within a nucleic acid sequence, comprising: a) determining the probability of each of one or more states for each nucleotide in the nucleic acid sequence based upon a bias, wherein each of the states is either a coding state or a noncoding state; b) setting a length for a window; c) determining which state has a maximum mean probability for the nucleic acid sequence on a first side of a middle nucleotide in the window, wherein the window begins at a first nucleotide; d) determining which state has a maximum mean probability for the nucleic acid sequence on a second side of the middle nucleotide in the window; e) determining that a deletion or insertion occurred at the middle nucleotide if i) the state with the maximum mean probability on the first side of the middle nucleotide is different from the state with the maximum mean probability on the second side of middle nucleotide, and ii) either an average of hypothetical state probabilities for the window with an insertion at the middle nucleotide or an average of hypothetical state probabilities for the window with a deletion at the middle nucleotide is greater than a sum of the middle nucleotide's coding states probabilities; and, f) repeating steps c) through e) for each remaining nucleotide in the nucleic acid sequence after the first nucleotide, wherein the window begins at each remaining nucleotide in turn.

The present invention includes and provides a method for determining exon location within a nucleic acid sequence, comprising a) determining the probability of each of one or more states for each nucleotide in the nucleic acid sequence based upon a bias, wherein each of the states is either a coding state or noncoding state; b) determining the coding strand of the nucleic acid sequence; c) determining the extent of an open reading frame within the nucleic acid sequence; d) classifying each nucleotide in a coding class or a noncoding class based on a most probable state for the coding strand; e)

reclassifying each nucleotide according to defined rules; and, f) determining that regions of the nucleic acid sequence in the coding class are exons.

The present invention includes and provides a program storage device readable by a machine, tangibly embodying a program of instructions executable by a machine to perform method steps to determine a probability for each of one or more states for a nucleotide in a nucleic acid sequence, the method steps comprising: a) determining an initial oligonucleotide probability for each of the states for an initial oligonucleotide in the nucleic acid sequence; b) determining transition probabilities for each of the states for nucleotides within the nucleic acid sequence following the initial oligonucleotide; c) determining a probability for the nucleic acid sequence for each of the states; and, d) determining a probability for each of the states for the nucleotide based upon the probability of the nucleic acid sequence and a bias.

The present invention includes and provides a program storage device readable by a machine, tangibly embodying a program of instructions executable by a machine to perform method steps to determine a probability for one or more states for more than one nucleotide in a nucleic acid sequence, the method steps comprising: a) determining an initial oligonucleotide probability for each of the states for an initial oligonucleotide in a window of a first nucleotide; b) determining transition probabilities for each of the states for nucleotides within the window following the initial oligonucleotide; c) determining a probability for the window for each of the states; d) determining a probability for each of the states for the nucleotide based upon the probability for the window and a bias; and, e) repeating steps a) through d) for each remaining nucleotide in the nucleic acid sequence.

The present invention includes and provides a program storage device readable by a machine, tangibly embodying a program of instructions executable by a machine to perform method steps to determine strand coding of a nucleic acid sequence, the method steps comprising: a) determining a probability of each of one or more states for each nucleotide in the nucleic acid sequence based upon a bias, wherein each of the states is either a positive strand state or a negative strand state; b) summing the probabilities of the positive strand states for each of the nucleotides to produce a sum of probabilities for positive states; c) summing the probabilities of the negative strand states for each of the nucleotides to produce a sum of probabilities for negative states; and, d) deciding one of i) coding is mixed or not detectable if a first function of the sum of probabilities for positive states and the sum of probabilities for negative states is less than a threshold value; ii) coding is on the positive strand if a second function of the sum of probabilities for positive states is greater than a third function of the sum of probabilities for negative states and the first function is not less than the threshold value; and iii) coding is on the negative strand if the second function of the sum of probabilities for positive states is not greater than the third function of the sum of probabilities for negative states and the first function is not less than the threshold value.

The present invention includes and provides a program storage device readable by a machine, tangibly embodying a program of instructions executable by a machine to perform method steps to determine the extent of an open reading frame within a nucleic acid sequence, the method steps comprising: a) determining the probability of each of one or more states for each nucleotide in the nucleic acid sequence based upon a bias, wherein each of the states is either a coding state or a noncoding state; b) determining the coding strand of the nucleic acid sequence; and, c) determining the points within the nucleic acid sequence in the coding strand at which the sum of the probabilities of the coding states for each nucleotide drops below a first threshold value for a number of nucleotides greater than a second threshold value, wherein ends of the open reading frame are indicated at the points.

The present invention includes and provides a program storage device readable by a machine, tangibly embodying a program of instructions executable by a machine to perform method steps to determine the location of insertions and deletions within a nucleic acid sequence, the method steps comprising: a) determining the probability of each of one or more states for each nucleotide in the nucleic acid sequence based upon a bias, wherein each of the states is either a coding state or a noncoding state; b) setting a length for a window; c) determining which state has a maximum mean probability for the nucleic acid sequence on a first side of a middle nucleotide in the window, wherein the window begins at a first nucleotide; d) determining which state has a maximum mean probability for the nucleic acid sequence on a second side of the middle nucleotide in the window; e) determining that a deletion or insertion occurred at the middle nucleotide if i) the state with the maximum mean probability on the first side of the middle nucleotide is different from the state with the maximum mean probability on the second side of middle nucleotide, and ii) either an average of hypothetical state probabilities for the window with an insertion at the middle nucleotide or an average of hypothetical state probabilities for the window with a deletion at the middle nucleotide is greater than a sum of the middle nucleotide's coding states probabilities; and, f) repeating steps c) through e) for each remaining nucleotide in the nucleic acid sequence after the first nucleotide, wherein the window begins at each remaining nucleotide in turn.

The present invention includes and provides a program storage device readable by a machine, tangibly embodying a program of instructions executable by a machine to perform method steps to determine exon location within a nucleic acid sequence, the method steps comprising: a) determining the probability of each of one or more states for each nucleotide in the nucleic acid sequence based upon a bias, wherein each of the states is either a coding state or noncoding state; b) determining the coding strand of the nucleic acid sequence; c) determining the extent of an open reading frame within the nucleic acid sequence; d) classifying each nucleotide in a coding class or a noncoding class based on a most probable state for the coding strand; e) reclassifying each nucleotide according to defined rules; and, f) determining that regions of the nucleic acid sequence in the coding class are exons.

The present invention includes and provides a computer system for determining a probability for each of one or more states for a nucleotide in a nucleic acid sequence, comprising: an input device for inputting the nucleic acid sequence; a memory for storing the nucleic acid sequence; a processing unit configured for retrieving the nucleic acid sequence and for: a) determining an initial oligonucleotide probability for each of the states for an initial oligonucleotide in the nucleic acid sequence; b) determining transition probabilities for each of the states for nucleotides within the nucleic acid sequence following the initial oligonucleotide; c) determining a probability for the nucleic acid sequence for each of the states; and, d) determining a probability for each of the states for the nucleotide based upon the probability of the nucleic acid sequence and a bias.

The present invention includes and provides a computer system for determining a probability for each of one or more states for more than one nucleotide in a nucleic acid sequence, comprising: an input device for inputting the nucleic acid sequence; a memory for storing the nucleic acid sequence; a processing unit configured for retrieving the nucleic acid sequence and for: a) determining an initial oligonucleotide probability for each of the states for an initial oligonucleotide in a window of a first nucleotide; b) determining transition probabilities for each of the states for nucleotides within the window following the initial oligonucleotide; c) determining a probability for the window for each of the states; d) determining a probability for each of the states for the nucleotide based upon the probability for the window and a bias; and, e) repeating steps a) through d) for each remaining nucleotide in the nucleic acid sequence.

The present invention includes and provides a computer system for determining strand coding of a nucleic acid sequence, comprising: an input device for inputting the nucleic acid sequence; a memory for storing the nucleic acid sequence; a processing unit configured for retrieving the nucleic acid sequence and for: a) determining a probability of each of one or more states for each nucleotide in the nucleic acid sequence based upon a bias, wherein each of the states is either a positive strand state or a negative strand state; b) summing die probabilities of the positive strand states for each of the nucleotides to produce a sum of probabilities for positive states; c) summing the probabilities of the negative strand states for each of the nucleotides to produce a sum of probabilities for negative states; and, d) deciding one of i) coding is mixed or not detectable if a first function of the sum of probabilities for positive states and the sum of probabilities for negative states is less than a threshold value; ii) coding is on the positive strand if a second function of the sum of probabilities for positive states is greater than a third function of the sum of probabilities for negative states and the first function is not less than the threshold value; and iii) coding is on the negative strand if the second function of the sum of probabilities for positive states is not greater than the third function of the sum of probabilities for negative states and the first function is not less than the threshold value.

The present invention includes and provides a computer system for determining the extent of an open reading frame within a nucleic acid sequence, comprising: an input device for inputting a nucleic acid sequence; a memory for storing the nucleic acid sequence; a processing unit configured for retrieving the nucleic acid sequence and for: a) determining the probability of each of one or more states for each nucleotide in the nucleic acid sequence based upon a bias, wherein each of the states is either a coding state or a noncoding state; b) determining the coding strand of the nucleic acid sequence; and, c) determining the points within the nucleic acid sequence in the coding strand at which the sum of the probabilities of the coding states for each nucleotide drops below a first threshold value for a number of nucleotides greater than a second threshold value, wherein ends of the open reading frame are indicated at the points.

The present invention includes and provides a computer system for determining the location of insertions and deletions within a nucleic acid sequence, comprising: an input device for inputting a nucleic acid sequence; a memory for storing the nucleic acid sequence; a processing unit configured for retrieving the nucleic acid sequence and for: a) determining the probability of each of one or more states for each nucleotide in the nucleic acid sequence based upon a bias, wherein each of the states is either a coding state or a noncoding state; b) setting a length for a window; c) determining which state has a maximum mean probability for the nucleic acid sequence on a first side of a middle nucleotide in the window, wherein the window begins at a first nucleotide; d) determining which state has a maximum mean probability for the nucleic acid sequence on a second side of the middle nucleotide in the window; e) determining that a deletion or insertion occurred at the middle nucleotide if i) the state with the maximum mean probability on the first side of the middle nucleotide is different from the state with the maximum mean probability on the second side of middle nucleotide, and ii) either an average of hypothetical state probabilities for the window with an insertion at the middle nucleotide or an average of hypothetical state probabilities for the window with a deletion at the middle nucleotide is greater than a sum of the middle nucleotide's coding states probabilities; and, f) repeating steps c) through e) for each remaining nucleotide in the nucleic acid sequence after the first nucleotide, wherein the window begins at each remaining nucleotide in turn.

The present invention includes and provides a computer system for determining exon location within a nucleic acid sequence, comprising: an input device for inputting a nucleic acid sequence; a memory for storing the nucleic acid sequence; a processing unit configured for retrieving the nucleic acid sequence and for: a) determining the probability of each of one or more states for each nucleotide in the nucleic acid sequence based upon a bias, wherein each of the states is either a coding state or noncoding state; b) determining the coding strand of the nucleic acid sequence; c) determining the extent of an open reading frame within the nucleic acid sequence; d) classifying each nucleotide in a coding class or a noncoding class based on a most probable state for the coding strand; e) reclassifying each nucleotide according to defined rules; and, f) determining that regions of the nucleic acid sequence in the coding class are exons.

The present invention includes and provides a computer program product comprising a computer usable medium having computer program logic recorded thereon for enabling a processor in a computer system to determine a probability for each of one or more states for a nucleotide in a nucleic acid sequence, the computer program logic comprising means for enabling the processor to perform each of the following steps: a) determining an initial oligonucleotide probability for each of the states for an initial oligonucleotide in the nucleic acid sequence; b) determining transition probabilities for each of the states for nucleotides within the nucleic acid sequence following the initial oligonucleotide; c) determining a probability for the nucleic acid sequence for each of the states; and, d) determining a probability for each of the states for the nucleotide based upon the probability of the nucleic acid sequence and a bias.

The present invention includes and provides a computer program product comprising a computer usable medium having computer program logic recorded thereon for enabling a processor in a computer system to determine a probability for each of one or more states for more than one nucleotide in a nucleic acid sequence, the computer program logic comprising means for enabling the processor to perform each of the following steps: a) determining an initial oligonucleotide probability for each of the states for an initial oligonucleotide in a window of a first nucleotide; b) determining transition probabilities for each of the states for nucleotides within the window following the initial oligonucleotide; c) determining a probability for the window for each of the states; d) determining a probability for each of the states for the nucleotide based upon the probability for the window and a bias; and, e) repeating steps a) through d) for each remaining nucleotide in the nucleic acid sequence.

The present invention includes and provides a computer program product comprising a computer usable medium having computer program logic recorded thereon for enabling a processor in a computer system to determine strand coding of a nucleic acid sequence, the computer program logic comprising means for enabling the processor to perform each of the following steps: a) determining a probability of each of one or more states for each nucleotide in the nucleic acid sequence based upon a bias, wherein each of the states is either a positive strand state or a negative strand state; b) summing the probabilities of the positive strand states for each of the nucleotides to produce a sum of probabilities for positive states; c) summing the probabilities of the negative strand states for each of the nucleotides to produce a sum of probabilities for negative states; and, d) deciding one of i) coding is mixed or not detectable if a first function of the sum of probabilities for positive states and the sum of probabilities for negative states is less than a threshold value; ii) coding is on the positive strand if a second function of the sum of probabilities for positive states is greater than a third function of the sum of probabilities for negative states and the first function is not less than the threshold value; and iii) coding is on the negative strand if the second function of the sum of probabilities for positive states is not greater than the third function of the sum of probabilities for negative states and the first function is not less than the threshold value.

The present invention includes and provides a computer program product comprising a computer usable medium having computer program logic recorded thereon for enabling a processor in a computer system to determine the extent of an open reading frame within a nucleic acid sequence, the computer program logic comprising means for enabling the processor to perform each of the following steps: a) determining the probability of each of one or more states for each nucleotide in the nucleic acid sequence based upon a bias, wherein each of the states is either a coding state or a noncoding state; b) determining the coding strand of the nucleic acid sequence; and, c) determining the points within the nucleic acid sequence in the coding strand at which the sum of the probabilities of the coding states for each nucleotide drops below a first threshold value for a number of nucleotides greater than a second threshold value, wherein ends of the open reading frame are indicated at the points.

The present invention includes and provides a computer program product comprising a computer usable medium having computer program logic recorded thereon for enabling a processor in a computer system to determine the location of insertions and deletions within a nucleic acid sequence, the computer program logic comprising means for enabling the processor to perform each of the following steps: a) determining the probability of each of one or more states for each nucleotide in the nucleic acid sequence based upon a bias, wherein each of the states is either a coding state or a noncoding state; b) setting a length for a window; c) determining which state has a maximum mean probability for the nucleic acid sequence on a first side of a middle nucleotide in the window, wherein the window begins at a first nucleotide; d) determining which state has a maximum mean probability for the nucleic acid sequence on a second side of the middle nucleotide in the window; e) determining that a deletion or insertion occurred at the middle nucleotide if i) the state with the maximum mean probability on the first side of the middle nucleotide is different from the state with the maximum mean probability on the second side of middle nucleotide, and ii) either an average of hypothetical state probabilities for the window with an insertion at the middle nucleotide or an average of hypothetical state probabilities for the window with a deletion at the middle nucleotide is greater than a sum of the middle nucleotide's coding states probabilities; and, f) repeating steps c) through e) for each remaining nucleotide in the nucleic acid sequence after the first nucleotide, wherein the window begins at each remaining nucleotide in turn.

The present invention includes and provides a computer program product comprising a computer usable medium having computer program logic recorded thereon for enabling a processor in a computer system to determine exon location within a nucleic acid sequence, the computer program logic comprising means for enabling the processor to perform each of the following steps: a) determining the probability of each of one or more states for each nucleotide in the nucleic acid sequence based upon a bias, wherein each of the states is either a coding state or noncoding state; b) determining the coding strand of the nucleic acid sequence; c) determining the extent of an open reading frame within the nucleic acid sequence; d) classifying each nucleotide in a coding class or a noncoding class based on a most probable state for the coding strand; e) reclassifying each nucleotide according to defined rules; and, f) determining that regions of the nucleic acid sequence in the coding class are exons.

The present invention includes and provides a method for determining a probability for one or more states for a nucleotide in a nucleic acid sequence, comprising determining a probability for each of the states for the nucleotide based upon a probability of the nucleic acid sequence and a bias.

The present invention includes and provides a method for determining a probability for each of one or more states for more than one nucleotide in a nucleic acid sequence comprising: a) determining a probability for each of the states for a first nucleotide in the nucleic acid sequence based upon a probability of a window in which the first nucleotide is located and a bias; and, b) repeating step a) for the remaining nucleotides in the nucleic acid sequence.

DETAILED DESCRIPTION OF THE INVENTION

Figure 1:
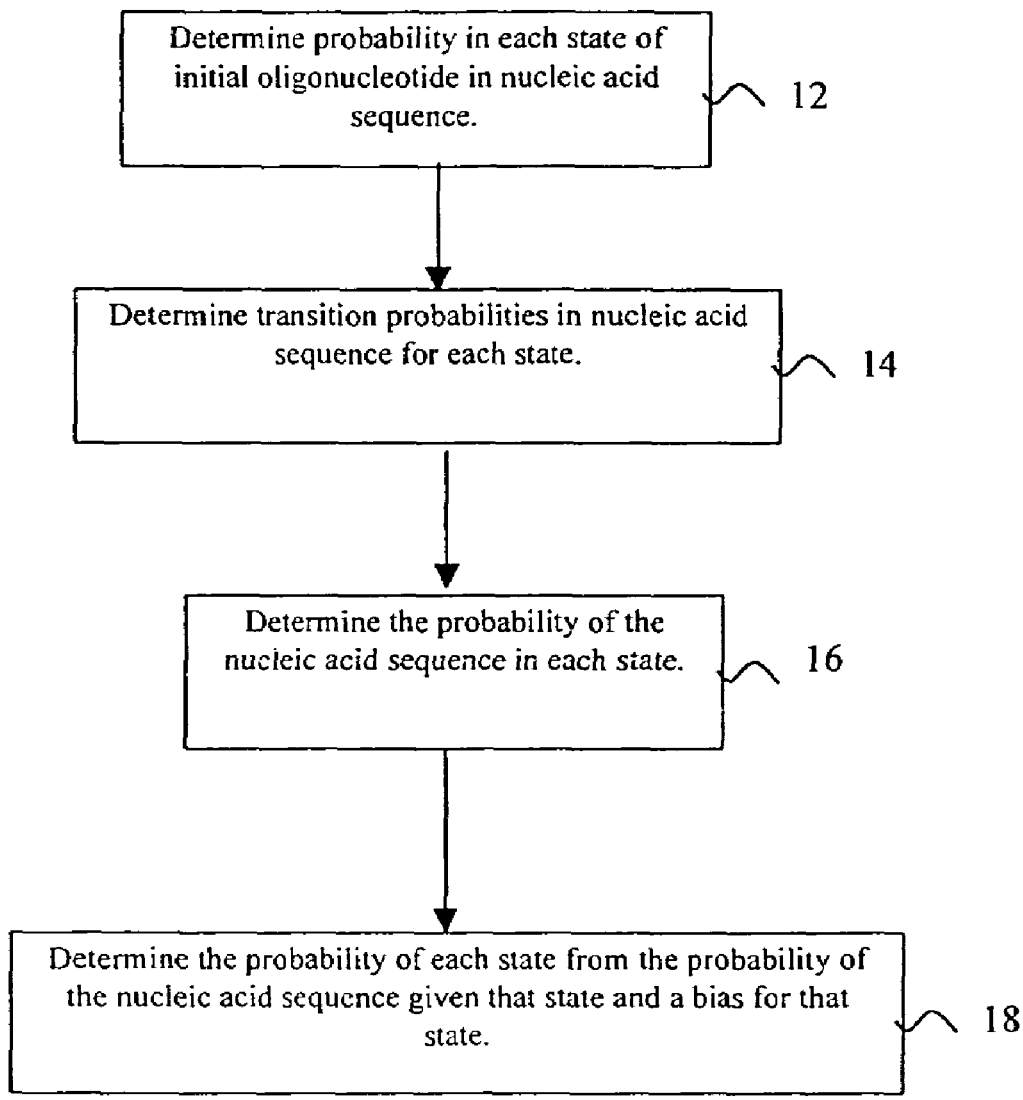
FIG. 1 is a flow chart representing one embodiment of a method for determining the probability of each of the possible states for a single nucleotide in a nucleic acid sequence.

Described herein are methods for determining the state probabilities of one or more nucleotides in a nucleic acid sequence, the coding strand of a nucleic acid sequence, the extent of an open reading frame in a nucleic acid sequence, the location of deletions and insertions in a nucleic acid sequence, the location of exons in a nucleic acid sequence, and the translation of those exons. Also described are program storage devices readable by a machine, tangibly embodying a program of instructions executable by a machine to perform the above methods. Also described are computer systems for implementing the above methods, comprising an input device for inputting a nucleic acid sequence, a memory for storing the nucleic acid sequence, and a processing unit. Also described are computer program products comprising a computer usable medium having computer program logic recorded thereon for enabling a processor in a computer system to perform the above methods.

Definitions:

Nucleic Acid Sequence—As used herein, "nucleic acid sequence" includes a nucleic acid sequence of any nucleic acid as is generally understood in the art. The nucleic acid can be DNA, cDNA, genomic DNA, raw DNA, expressed nucleic acid sequence tags (ESTs), RNA, mRNA, unprocessed RNA, processed RNA, or any other form of nucleic acid, regardless of whether or not the nucleic acid actually codes for a protein.

Nucleic acid sequences can be derived from any natural or artificial source, including prokaryotic and eukaryotic organisms, and can be at any stage of processing.

It is understood by those skilled in the art that any representation of a nucleic acid sequence is contemplated herein and within the scope of the present invention. That is, while conventionally nucleic acid sequences are represented by the nucleotide or base letters A, T, G, C, U, any alphanumeric or other representation of nucleotide or base nucleic acid sequence, whether digitally represented or otherwise, is within the scope of this invention. Further, nucleic acid sequence notation indicating uncertainty with respect to the identification of one or more bases in a nucleic acid sequence, for example IUB nomenclature such as R=G and A, Y=T and C, etc., can be incorporated into the method described herein and is within the scope of this invention.

Nucleic acid sequences having modified or non-standard bases can be incorporated into the method described herein and are within the scope of this invention. For the purposes of this invention, a nucleic acid sequence of "bases" is an equivalent nucleic acid sequence to the nucleic acid sequence in which the bases are found.

Reading frame—A "reading frame" is one of the possible phases in which one can read a sequence of codons (groups of three nucleotides) that can make up a coding region of DNA or RNA. In a codon the positions in 5' to 3' order are called the "first", "second", and "third" reading frames.

States—The "states" attributable to a nucleotide are the potential permutations of all of the possible reading frames and the two nucleic acid strands included in the probability model being used. A "+" is used to indicate the positive strand, and "−" to indicate the reverse compliment DNA strand. In a preferred embodiment, the possible states of any one nucleotide are positive strand first reading frame (1+), positive strand second reading frame (2+), positive strand third reading frame (3+), negative strand first reading frame (1−), negative strand second reading frame (2−), negative strand third reading frame (3−), positive strand noncoding (N+), and negative strand noncoding (N−). In another embodiment, the states can be, for example, just the four positive states listed above. Stated symbolically, "f" is an element in the set of states, i.e. $f \in \{1+, 2+, 3+, N+, 1-, 2-, 3-, N-\}$.

Coding State—A "coding state" is any of the states 1+, 2+, 3+, 1−, 2−, or 3−, which indicate coding, i.e. nucleic acids translated into protein.

Noncoding state—A "noncoding state" is either of the states N− or N+, both of which indicate noncoding, i.e. no protein translation.

Sequentially—"Sequentially" means performing a step or series of steps on nucleotides in order as the nucleotides occur in the nucleic acid sequence, in either direction.

State probabilities—The "state probabilities" of a nucleotide within a nucleic acid sequence are a vector of probabilities associated with the given nucleotide being in each of the states.

Window—A "window" is a contiguous and defined number of nucleotides within a nucleic acid sequence. For example, in a nucleic acid sequence having a length of several thousand nucleotides, a window of, again for example, 100 nucleotides can be defined for specific analysis at any place within the larger nucleic acid sequence.

Middle Nucleotide—The "middle nucleotide" in any given nucleic acid sequence or window is the nucleotide found at the numerical middle of the nucleic acid sequence or window, respectively, wherein the length of a nucleic acid sequence or window is the total number of nucleotides in the nucleic acid sequence or window. If the nucleic acid sequence or window has an even number of nucleotides, then the middle nucleotide can be either of the two nucleotides adjacent the numerical middle of the nucleic acid sequence or window. For example, the middle nucleotide in a 101 nucleotide long window is nucleotide number 51, and the middle nucleotide in a 100 nucleotide long window can be either nucleotide number 50 or nucleotide number 51.

Oligonucleotide—An "oligonucleotide" is a a series of contiguous nucleotides with a defined length.

Initial Oligonucleotide—The "initial oligonucleotide" is the oligonucleotide that occurs at the beginning of the nucleic acid sequence or window being examined. Therefore, the first nucleotide in the initial oligonucleotide is also the first nucleotide in the sequence or window.

Transition Probability—A "transition probability" for a given nucleotide is the probability of the nucleotide occurring given the oligonucleotide immediately preceding that nucleotide.

Bias Function—The "Bias Function" is a function that is used to differentialy alter the probability of one or more states of one or more nucleotides in a nucleic acid sequence. For example, if a region of the nucleic acid sequence under study is thought to be a coding region, then the bias function can be used to increase the calculated probability of the coding states for that nucleic acid sequence.

Bias—"Bias" is a set of one or more values that are used in the Bias Function, and is used to alter the probability of one or more states of one or more nucleotides in a nucleic acid sequence.

Filter—A "filter" as used herein is any method or algorithm for unifying and making more homogeneous regions of a nucleic acid sequence that have been classified in disparate states. A filter is used for the purpose of more clearly defining coding region boundaries in a nucleic acid sequence. In a method, a step in which a filter is applied is a "filtering step."

Class—A "class" of nucleotides is a group of nucleotides that are designated as having one state for the purposes of filtering.

Positive Strand and Negative Strand—The terms "positive strand (+)" and "negative strand (−)" represent complementary nucleic acid sequences. The sequence in one strand is defined by the sequence in the complementary strand.

Positive Strand State—A "positive strand state" is any of states 1+, 2+, 3+, N+.

Negative Strand State—A "negative strand state" is any of states 1−, 2−, 3−, N−.

Description

The methods described herein can be performed in any manner that allows for the analysis of the nucleic acid sequence under study and computation of the probabilities associated with that nucleic acid sequence. In a preferred embodiment, the physical nucleic acid sequence, for example a DNA sequence having a contiguous nucleic acid sequence of G, C, T, and A nucleotides, is converted into digital form by, for example, inputting the nucleic acid sequence into a computer system. The computer then processes the nucleic acid sequence using the methods described herein. Any nucleic acid sequence referred to herein can be arranged to have a beginning and an end, and numbered so that the first nucleotide in the nucleic acid sequence is number 1, the next nucleotide in the nucleic acid sequence is number 2, and so on until the end of the nucleic acid sequence. Any other numbering scheme that is useful can be used.

The methods shown in FIGS. 1-7 are independent, and, although several of the methods described can be utilized together, they can each be performed as independent methods. Further, where one method calls for a step in which one of the other methods can be used for that step, the use of the other method in the step represents only one embodiment, and other methods for performing the step can be used as well.

Any probability model applicable to nucleic acid sequence state probabilities can be used for the probability steps if the output of the probability model sufficiently supports the method, including inhomogeneous Markov models that have fewer than eight states, for example, those having only six or four states. In a preferred embodiment, the inhomogeneous Markov model has eight states. (For a general discussion of various models, see Durbin, et al., Biological Sequence Analysis (1998), which is herein incorporated by reference in its entirety).

Any nucleic acid sequence source can be used, regardless of the accuracy of the nucleic acid sequence relative to the physical molecule it represents, including raw nucleic acid sequence data and nucleic acid sequence data that has been changed or adjusted for other purposes, such as nucleic acid sequences that have been filtered to improve accuracy, nucleic acid sequences that have been altered to account for known mutations, and nucleic acid sequences that have been engineered in any manner whatsoever, among others. Nucleic acid sequence information produced by automated nucleic acid sequencers can be used, as well as nucleic acid sequence information derived by any conventional sequencing technique, such as dideoxy sequencing, among others. Nucleic acid sequences produced by or from other bioinformatic processing methods or nucleic acid databases can be used, for example, including nucleic acid sequences stored in public access databases such as GenBank. Although nucleic acid sequences with any amount of error can be used, in a preferred embodiment the amount of sequencing error present is less than about 15%, and more preferably is less than about 10%. However, an advantage of the methods of the present invention is that they can utilize lower quality nucleic acid sequences. In this embodiment, the methods of the present invention can utilize nucleic acid sequences where the average sequence accuracy is less than 99%, more preferably less than 95%, more preferably less than 90, 80, or 70%.

The present invention includes the incorporation of bias into probability models that determine state probabilities for one or more nucleotides. The bias is used to alter the statistical probability of one or more states for a nucleotide. A bias of zero, for example, will reduce the probability of a state to zero, while a bias of one will not alter the statistical probability. Values greater than one will increase the statistical probability of a state, while values between zero and one will reduce the statistical probability of a state. Bias can be defined by the investigator in order to influence the probability of states. In a preferred embodiment, bias is defined to alter the probability of states in a manner consistent with existing knowledge of the nucleic acid sequence under study. For example, if a nucleic acid sequence has a region that is strongly suspected to be coding, then the nucleotides in that region can be assigned a large bias for the coding states, and a small bias for the noncoding states. Bias can be incorporated into any conventional statistical model that provides a method for determining state probabilities in order to allow for the biasing of statistical probabilities in that model. In one embodiment, bias can be defined for each state as a number equal to or greater than zero, excluding 1. In this embodiment, the statistical probability of a state will be reduced if the bias is set to a number equal to or greater than zero and less than one, and increased if the bias is set to a number greater than one, and all states are biases in one direction or the other. In another embodiment, bias can be defined as one for one or more states, and a number other than one for one or more states. In this embodiment, one or more states has a defined bias of one, which results in no biasing of the probability of that state, while one or more states have a defined value equal to or greater than zero, excluding one. In this embodiment, one or more states are biased, and one or more states are not. In a preferred embodiment, the bias is between 0.0 and 0.9 or greater than 1.1.

FIG. 1 represents one embodiment of the method of the present invention for determining the state probabilities of a single nucleotide within a nucleic acid sequence. The nucleotide for which the state probabilities are determined can be any nucleotide in the nucleic acid sequence, preferably is a nucleotide close to the middle of the sequence, and in a preferred embodiment the nucleotide is the middle nucleotide in the nucleic acid sequence. It is preferable to determine state probabilities for a nucleotide at or near the middle of the nucleic acid sequence. State probabilities for the nucleotide are determined by first finding the probability of the initial oligonucleotide in the nucleic acid sequence, and then finding the transition probabilities for the remainder of the nucleotides in the nucleic acid sequence. The initial oligonucleotide probability and transition probability information is used to determine the probabilities of each of the states for the entire nucleic acid sequence, and the resulting state probabilities are assigned to the nucleotide. Eight states are described below for FIG. 1, but those of skill in the art will readily see that fewer than eight states can be employed.

Referring now to FIG. 1, in step 12, the probability that the initial oligonucleotide occurs in each of the states is determined according to equation I:

$$P_f(a_1 \ldots a_k) = \frac{|a_1 \ldots a_k|_f}{N_f} \quad (I)$$

where "$a_1 \ldots a_k$" is an initial oligonucleotide of length k, $a_1$ is the first nucleotide in the oligonucleotide, $N_f$ is the set of all oligonucleotides occurring in the model sample set, and f is an element of the set of states, which, in a preferred embodiment, is $\{1+,2+,3+,N+,1-,2-,3-,N-\}$.

The oligonucleotide length is predefined, and can be any length for which probabilities can be reliably generated. Oligonucleotides can be, for example, from 2 to 100 nucleotides, preferably 5 to 20 nucleotides, and more preferably from 8 to 12 nucleotides in length. The initial oligonucleotide frequencies of all possible oligonucleotides in the model sample set can be, for example stored in a look up table, which is accessed as needed. A table defining the model sample set can be constructed, for example, by reference to sample nucleic acid sequences from a previously examined collection of nucleic acids, preferably from a closely related organism, more preferably from the same organism as the nucleic acid sequence under investigation. For example, sample nucleic acid sequences from *Arabidopsis* can be used for a table for investigation of nucleic acid sequences of plants such as soybean, maize, etc. Similarly, sample nucleic acid sequences from a chimpanzee can be used for a table for investigation of nucleic acid sequences of humans. By examining known nucleic acid sequences, model oligonucleotide frequencies in each of the states can be determined. A table can include indefinite or modified nucleotides, or any other nucleotide variations that occur in nucleic acid sequences. Alternatively, it is also possible to use estimation functions in place of such a table of probabilities (see, for example, Besemer, J., Borodovsky, M. (1999) *Nucl. Acids Res.*, v.27, pp. 3911-3920, which is herein incorporated by reference in its entirety).

In step 14, the transition probabilities for all nucleotides in the nucleic acid sequence after the initial oligonucleotide in each of the states are determined. The transition probability is the probability of a nucleotide occuring given the oligonucleotide immediately preceding the nucleotide. The transition probability for the first nucleotide transition is set out in equation II:

$$P_f(a_{k+1} | a_1 \ldots a_k) = \frac{|a_1 \ldots a_{k+1}|_f}{|a_1 \ldots a_k|_f} \quad (II)$$

where k is the oligonucleotide length, $a_1$ is the first nucleotide in the oligonucleotide, "$a_1 \ldots a_k$" is the initial oligonucleotide, $a_{k+1}$ is the nucleotide immediately following $a_k$, and $f \in \{1+,2+,3+,N+,1-,2-,3-,N-\}$. Equation II determines the transition probability for the first nucleotide following the initial oligonucleotide. After determining the transition probability for the first nucleotide after the initial oligonucleotide, the transition probabilities are determined sequentially for the remaining nucleotides in the nucleic acid sequence. This means that a transition probability is determined for the second nucleotide after the initial oligonucleotide ($a_{k+2}$) based on the oligonucleotide beginning at the second position, $a_2$, and ending at $a_{k+1}$. The 5 process is repeated until the end of the nucleic acid sequence is reached. For example, if the oligonucleotide length is ten, then a transition probability for nucleotide eleven is determined based on the oligonucleotide comprising nucleotides one through ten. Then, a transition probability for nucleotide twelve is determined based on the oligonucleotide comprising nucleotides two through eleven, and so on, until the last nucleotide in the nucleic acid sequence is reached.

The transition probabilities can be stored in a table, for example. The table can be constructed, for example, by reference to sample nucleic acid sequences from a previously examined portion of nucleic acid, preferably from a closely related organism, more preferably from the same organism as the nucleic acid under investigation. By examining known nucleic acid sequences, model transition probabilities in each of the states can be determined.

In step 16, the probability of the nucleic acid sequence, (S), occurring in each of the states (f) is determined by finding the product of the probability of the initial oligonucleotide and the transition probabilities in each of the states. This step is set forth in equation III for a model with eight states:

$$P_f(S) = P_f(a_1 \ldots a_k) \cdot \prod_{i=1}^{\omega} P_{F(i)}(a_{k+i+1} | a_i \ldots a_{i+k}) \quad (III)$$

where the function $$F(i) = \begin{cases} i \bmod 3 + 1 & \text{if } f = 1^\pm \\ (i+1) \bmod 3 + 1 & \text{if } f = 2^\pm \\ (i+2) \bmod 3 + 1 & \text{if } f = 3^\pm \\ N & \text{if } f = N^\pm \end{cases}$$

and ω is the length of the nucleic acid sequence, and "$a_1 \ldots a_k$" is the initial oligonucleotide.

In step 18, the probability of each state for the nucleic acid sequence "P(f|S)" is determined given the probability of the nucleic acid sequence, S, in each state. A bias function, $\phi(f)$, is incorporated into the equation to account for known nucleic acid sequence information. This step is set forth in equation IV:

$$P(f | S) = \frac{\phi(f) \cdot P_f \cdot P_f(S)}{\sum_{i \in \{1^+,2^+,3^+,N^+,1^-,2^-,3^-,N^-\}} \phi(f) \cdot P_i \cdot P_i(S)} \quad (IV)$$

wherein P$f$ is $$\frac{1}{12}$$

for each coding state (1+, 2+, 3+, 1−, 2−, 3−) and $$\frac{1}{4}$$

for each noncoding state (N+, N−). The bias function is used to modify these default P$f$ values. By modifying the default values, the investigator can account for known nucleic acid sequence features. For example, if another bioinformatics process has indicated that there is a high probability that a certain portion of a nucleic acid sequence comprises a gene, then it would be advantageous to bias the state probabilities in favor of the coding states. The resulting state probabilities produced by the method will reflect the bias through stronger probabilities of the coding states relative to the noncoding states.

If, for example, the nucleic acid sequence is known to be a coding nucleic acid sequence, the bias function can be defined by equation V:

$$\phi(f) = \begin{cases} 1 & \text{if } f \neq N^{\pm} \\ 0 & \text{if } f = N^{\pm} \end{cases} \quad (V)$$

Equation V uses a bias of 1 for all coding states, and a bias of 0 for all noncoding states. The net effect will be to cause the probability of the sequence in each noncoding state to drop to zero, while leaving the probability of the sequence in the coding states unaffected. Application of equation IV then leads to a decrease of the probabilities of the noncoding states to zero, while increasing the probabilities of the coding states.

If the nucleic acid sequence is known to be a noncoding nucleic acid sequence, then the bias function can be defined by equation VI:

$$\phi(f) = \begin{cases} 0 & \text{if } f \neq N^{\pm} \\ 1 & \text{if } f = N^{\pm} \end{cases} \quad (VI)$$

Equation VI reverses the effect of equation V. Of course, the bias function does not need to be binary in nature, as is shown in the above two examples, but rather can be defined in any manner that corresponds with known nucleic acid sequence data. A principal feature of this technique is that it can be used to specifically combine gene prediction information from other sources into biasing the results of the state probabilities algorithm shown in FIG. 1 (and subsequent gene prediction based thereon).

The resulting values for the probability of each state for the nucleic acid sequence can now be associated with the nucleotide for which state probabilities were being determined.

In a further embodiment of the method shown in FIG. 1, the nucleic acid sequence is part of a larger nucleic acid sequence. This embodiment can be applied to any of the methods described herein wherein a nucleic acid sequence is used, including those represented in FIGS. 1 through 7.

FIG. 1 shows the determination of state probabilities for a single nucleotide in a nucleic acid sequence. Oftentimes, however, it will be desirable to determine the state probabilities for more than one nucleotide in a nucleic acid sequence.

Figure 2:
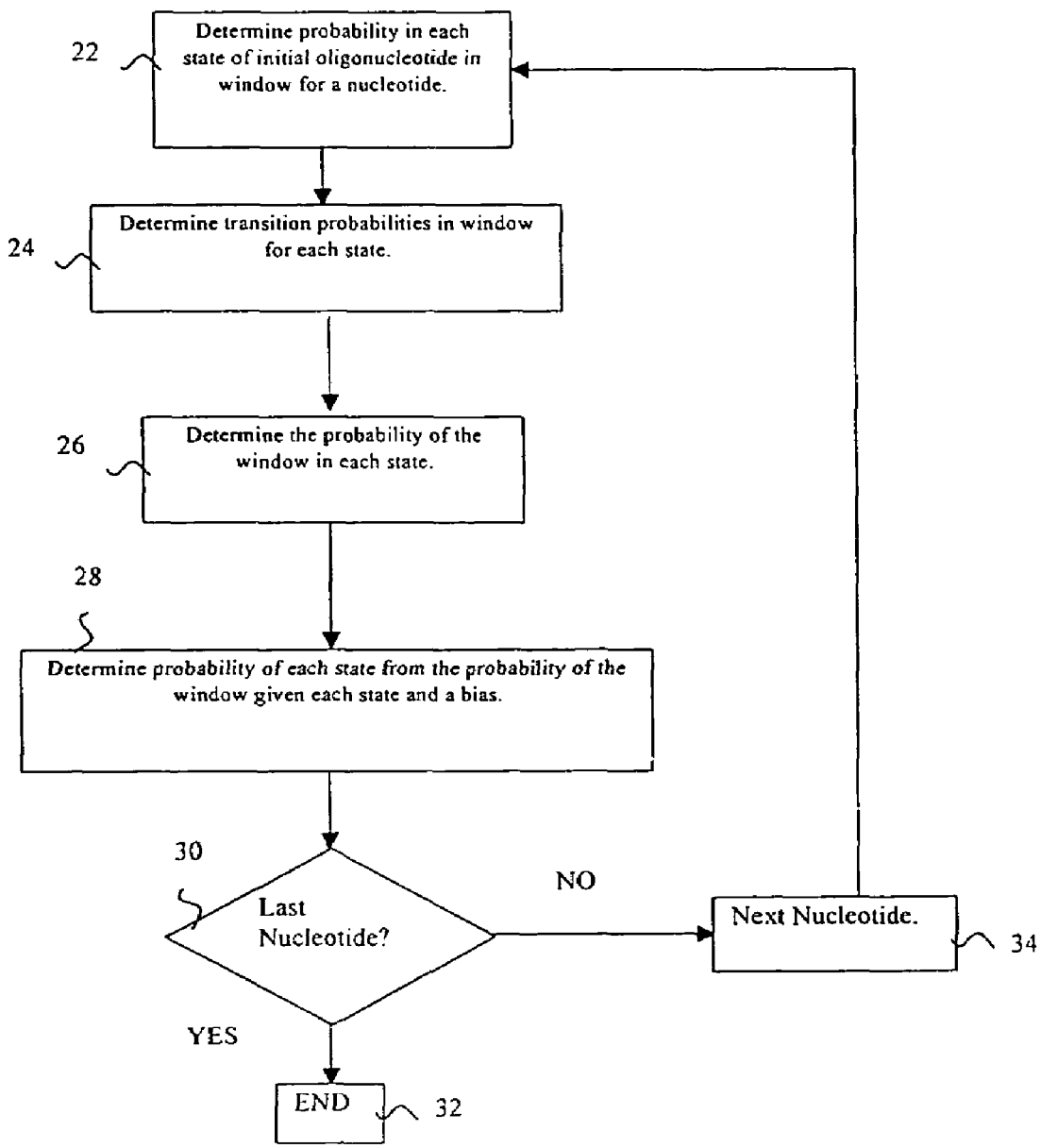
FIG. 2 is a flow chart representing one embodiment of a method for determining the probability of each of the possible states for a multiple nucleotides in a nucleic acid sequence.

FIG. 2 represents the application of the method shown in FIG. 1 to multiple nucleotides in a nucleic acid sequence. In order to determine the state probabilities for more than one nucleotide, a window is used for each nucleotide that is examined. The nucleotide that is being examined is within the window, and the probability determinations set out in equations I, II, III, and IV are performed for the sequence in the window. The oligonucleotide probabilities are determined as before for the nucleic acid sequence within the window, probabilities for each of the states are determined for the nucleic acid sequence within the window, and those probabilities are assigned to the nucleotide within the window for which state probabilities are being determined, which, in a preferred embodiment, is the middle nucleotide. Another nucleotide is then examined, with the window shifted or redefined around the new nucleotide, and so on, until the final nucleotide in the nucleic acid sequence for which state probabilities are to be determined is reached.

In steps 22, 24, 26, and 28, probabilities are determined as in steps 12, 14, 16, and 18 respectively, with the window in steps 22, 24, 26, and 28 corresponding to the nucleic acid sequence in steps 12, 14, 16, and 18 respectively for the purposes of those steps. At step 28, the state probabilities for the nucleotide for which state probabilities are being determined are associated with that nucleotide.

In step 30, the algorithm checks to see if the state probabilities for the last nucleotide have just been determined. If yes, flow proceeds to step 32 and ends. If in step 30 the last nucleotide has not been reached, flow proceeds to step 34, where the next nucleotide for which state probabilities are to be determined is designated as the nucleotide to analyze in steps 22, 24, 26, and 28. After step 34, flow returns to steps 22, 24, 26, and 28, where the state probabilities of the designated nucleotide are determined. At step 34 any nucleotide from the remaining nucleotides that have not yet had state probabilities determined can be designated the next nucleotide.

In a preferred embodiment, the first nucleotide to be examined in step 22 is the first nucleotide in a contiguous nucleic acid sequence of nucleotides for which state probabilities are to be determined, each subsequent nucleotide at step 34 is the next nucleotide of the contiguous nucleic acid sequence of nucleotides for which state probabilities are to be determined, and the last nucleotide in step 30 is the last nucleotide in the contiguous nucleic acid sequence of nucleotides for which state probabilities are to be determined.

The window size can be the same or different for each nucleotide, and the nucleotide can be located anywhere within its window. In a preferred embodiment, the window size is the same for each nucleotide in the nucleic acid sequence, and each nucleotide is the middle nucleotide in its own window. In one embodiment, windows are from 3 nucleotides to 1,000 nucleotides in length, preferably 50 to 200 nucleotides in length, and more preferably from 75 to 125 nucleotides in length.

The result of the process shown in FIG. 2 is the association of state probabilities with each individual nucleotide for which state probabilities were determined. In one embodiment, the nucleotides for which state probabilities are to be determined are a contiguous nucleic acid sequence of nucleotides within a longer nucleic acid sequence of nucleotides.

FIGS. 3 through 7 all utilize probability models to determine state probabilities. Any probability model that allows for determination of the required probabilities in a plurality of states can be used, with use of an inhomogeneous Markov model preferred, and use of the inhomogeneous Markov model described above in reference to FIG. 2 especially preferred.

Figure 3:
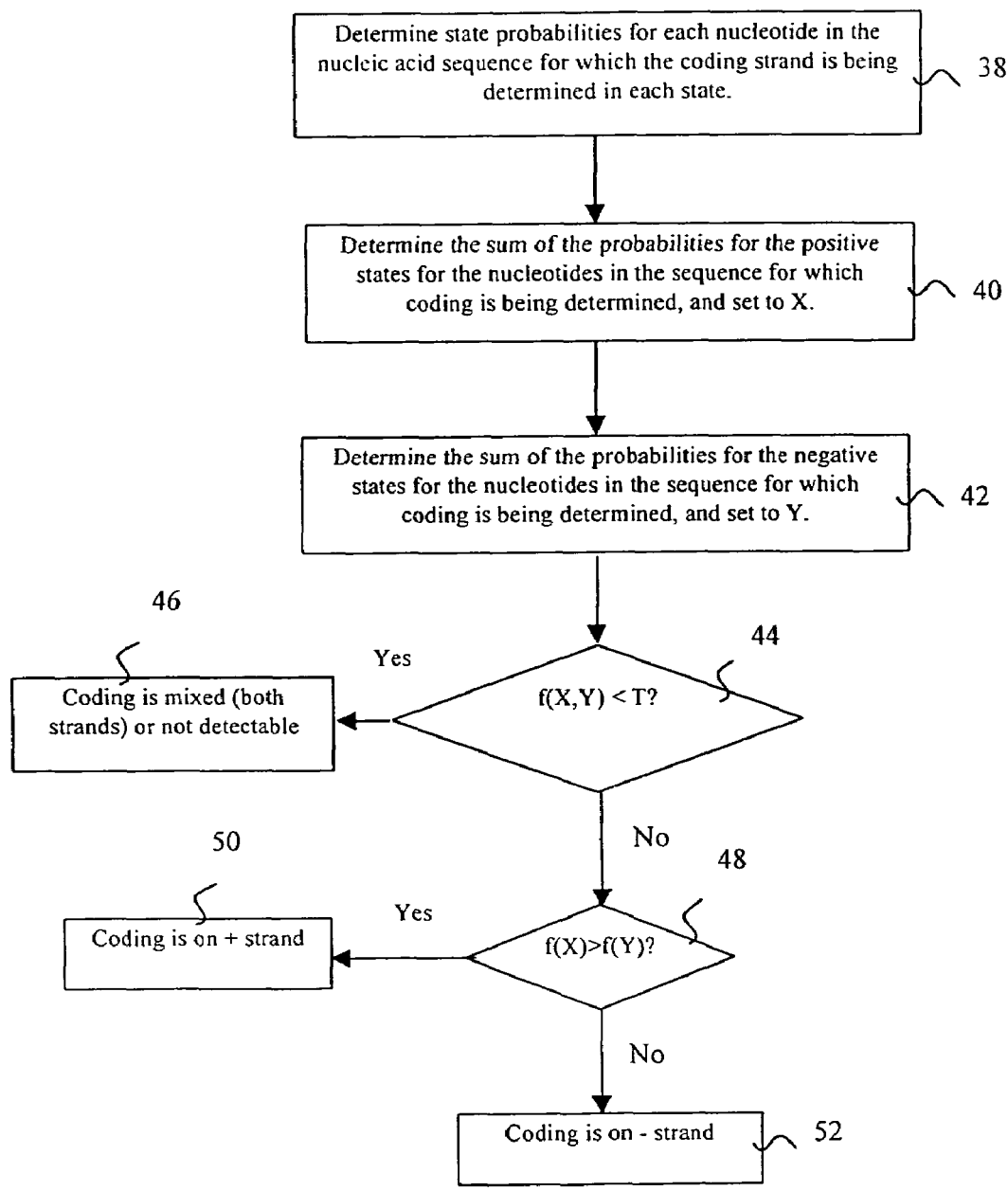
FIG. 3 is a flow chart representing one embodiment of a method for determining the coding strand of a nucleic acid sequence.

FIG. 3 represents one embodiment of a method for determining the coding strand of a nucleic acid sequence. The process determines the state probabilities for each nucleotide in the nucleic acid sequence, sums the positive states for the nucleic acid sequence, and sums the negative states for the nucleic acid sequence. If the sums for the positive states and the negative states are sufficiently different, then the process determines that the state with the greater sum is the coding strand.

In step 38, state probabilities are determined for each nucleotide in the nucleic acid sequence for which the coding strand is being determined. In one embodiment, state probabilities are determined using the inhomogeneous Markov model described above in reference to FIG. 2.

In step 40, the probability of each state determined in step 38 for the positive states (1+, 2+, 3+, and N+) for each nucleotide in the nucleic acid sequence for which the coding strand is being determined are summed. That is, the values for the states of noncoding, positive and coding, positive in the first, second, and third reading frames for all nucleotides in the nucleic acid sequence for which the coding strand is being determined are summed. The sum is set to the arbitrary variable X.

In step 42, the values determined in step 38 for the negative states (1−, 2−, 3−, N−) for each nucleotide in the nucleic acid sequence for which the coding strand is being determined are summed. That is, the values for the states of noncoding, negative and coding, negative in the first, second, and third reading frames for all nucleotides in the nucleic acid sequence for which the coding strand is being determined are summed. The sum is set to the arbitrary variable Y. Steps 40 and 42 can be performed in reverse order.

In step 44, a function of X and Y is used to determine whether the state probabilities indicate sufficient coding on one strand of the nucleic acid sequence. That is, it is determined whether f(X,Y)<T, where T is a defined threshold value. Any function can be used that allows for the desired discrimination. In one embodiment, the function used in step 44 is $$f(X, Y) = \frac{|X - Y|}{(X + Y)}. \text{ When } f(X, Y) = \frac{|X - Y|}{(X + Y)},$$

the value of T is about 0.1 to about 0.9, preferably is about 0.25 to about 0.75, and even more preferably is about 0.4 to about 0.6. If in step 44 the function results in a value that is less than the threshold value, T then flow proceeds to step 46, where it is determined that coding is mixed or is not detectable. If in step 44 the function results in a value that is equal to or greater than the threshold value, T, then flow proceeds to step 48.

In step 48, it is determined on which strand coding occurs. A function of X is compared to a function of Y to determine which strand is coding. Any two functions that allow for the proper comparison can be used, including functions that weight one of the two strands. In one embodiment, $f(X)=X$ and $f(Y)=Y$, and the comparison in step 48 simply determines which sum is greater. If in step 48 the function of X is found to be greater than the function of Y, then flow proceeds to step 50 where it is determined that coding is on the positive strand.

If in step 48 it is determined that the function of X is not greater than Y, then flow proceeds to step 52, where it is determined that coding is on the negative strand.

In another embodiment of the method represented by FIG. 3, steps 44 and 46 can be removed for situations in which it is already known or suspected that coding is present and only on one strand. In this embodiment, flow begins at step 38 and, after executing step 42, flow proceeds directly from step 42 to step 48.

Figure 4:
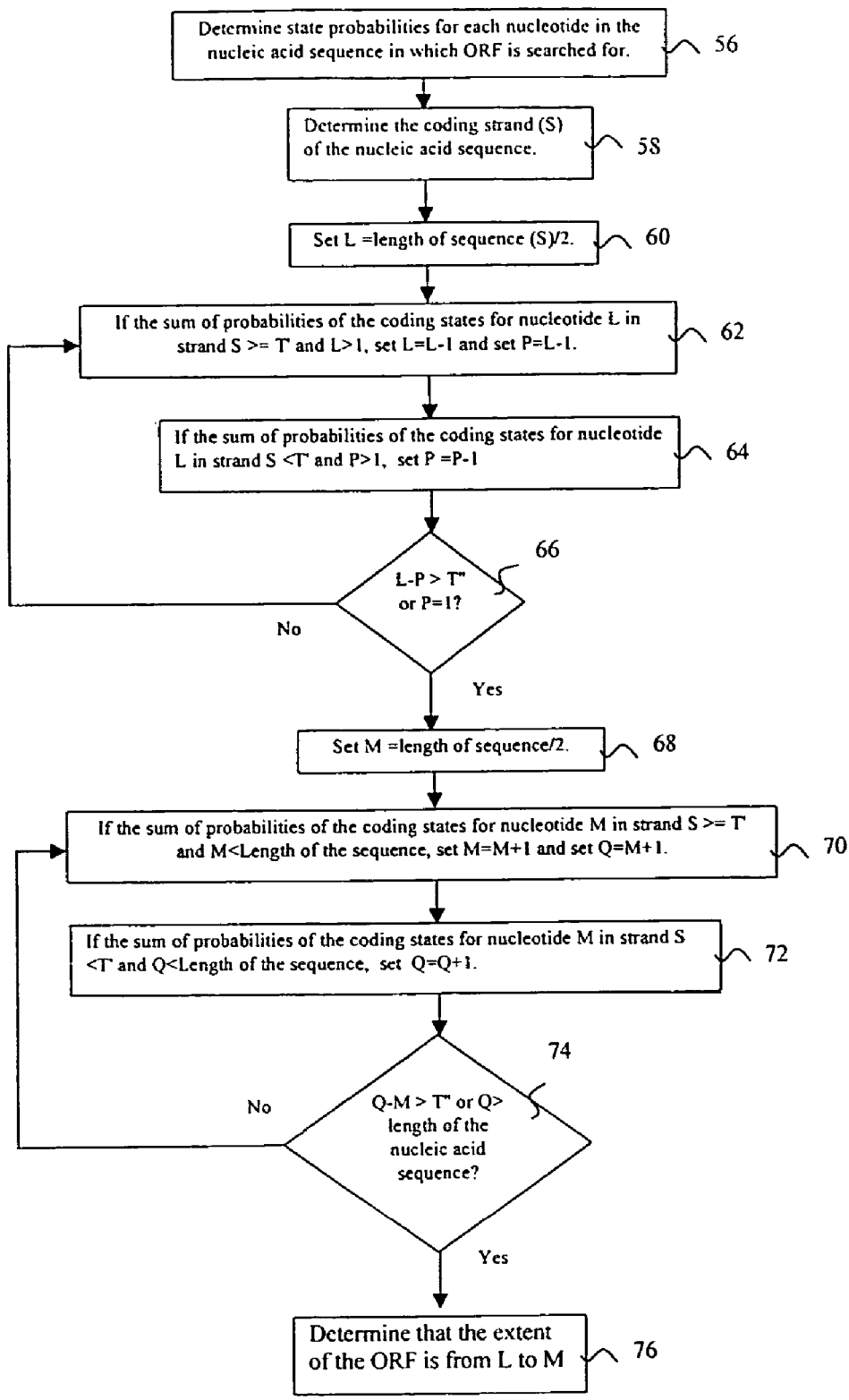
FIG. 4 is a flow chart representing one embodiment of a method for determining the extent of an open reading frame within a nucleic acid sequence.

FIG. 4 represents one embodiment of a method for determining the extent of an open reading frame (ORF) within a nucleic acid sequence. The process determines the extent of the open reading frame by first determining the state probabilities for each nucleotide in the nucleic acid sequence. Then, beginning from within the nucleic acid sequence, preferably the approximate middle of the nucleic acid sequence, and proceeding toward one end of the nucleic acid sequence, the process examines each nucleotide in turn and determines whether the nucleotide is sufficiently likely to code. When a sufficient number of nucleotides with an insufficient likelihood of coding are encountered, the process determines that one end of the open reading frame has been found. The process then repeats from the middle to the other end of the nucleic acid sequence in order to find the second end of the open reading frame.

In step 56, the state probabilities of each of the nucleotides in the nucleic acid sequence are determined. As stated above, any probability model that has the correct form of output can be used, with an inhomogeneous Markov model preferred, and the inhomogeneous Markov model described above and represented in FIG. 2 most preferred.

In step 58, the coding strand of the nucleic acid sequence is determined and designated "S." Any algorithm or method that can use the state probabilities produced in step 56 can be used, and in a preferred embodiment, the method described above and represented in FIG. 3 is used. If coding strand is indeterminate, an error can be returned at this step and processing does not continue. In applications where the coding strand is already known or suspected, step 58 can be omitted from the process, in which case step 56 can flow directly to step 60.

In step 60 an arbitrary variable, L, is set to half of the length of the nucleic acid sequence, S, which designates L the middle nucleotide (determination of the middle for even and odd sequences is done as described above for the middle nucleotide). In an alternative embodiment, L can initially be set to any nucleotide in the nucleic acid sequence. It is preferred, however, to begin with L relatively close to the middle of the putative ORF, because proper resolution of the ends of the ORF is then more likely.

Steps 62, 64, and 66 effectively search through the nucleic acid sequence in a descending direction from L toward the first nucleotide in the nucleic acid sequence for one of the ORF ends. In step 62, the sum of the probabilities of the coding states on the strand S—that is the set (1+, 2+, and 3+) or the set (1−, 2−, and 3−) depending on whether strand S is the positive or negative strand—for nucleotide L is determined and compared to threshold value T'. In an alternative embodiment, the probability of all six coding states (1+, 2+, 3+, 1−, 2−, and 3−) can be combined. If the sum of the coding states is greater than or equal to a threshold value, T', and the nucleotide is greater than the first nucleotide in the nucleic acid sequence (that is, L>1), then L is set to L−1 and P, an arbitrary counting variable, is set to L−1. In one embodiment, the value of T is about 0.1 to about 0.9, preferably is about 0.25 to about 0.75, and even more preferably is about 0.4 to about 0.6.

Flow then proceeds to step 64. If the sum of the coding states, as discussed above, is less than T' and P is greater than 1, then P is set to P−1. The effect of the two steps, 62 and 64, is to reduce both L and P at the same rate if the sum of the coding states is greater than or equal to T', or to reduce P but not L if the sum of the states is less than T'.

After step 64, flow proceeds to step 66, where it is determined if L−P>T" or P=1. If L−P>T", wherein T" is a threshold value, then a gap between the last nucleotide (L) with a sufficient sum of coding states and the current nucleotide being examined has increased beyond the threshold value T". T" can be set to any number that allows for the proper gap of noncoding nucleotides. T" should be larger than the maximum expected length of an intron for the nucleic acid sequence. This number will depend in large part on the model sample set being used. If the number for T" is set too low, then a relatively lengthy intron will be sufficient to fix L at the end of an exon that is not at the end of the ORF. If P=1, then the end of the sequence has been reached. In one embodiment, T" is about 10 to about 20,000 nucleotides, preferably about 50 to about 10,000 nucleotides, and more preferably about 500 to about 700 nucleotides.

If neither condition in step 66 is met, then flow returns to step 62 and loops through steps 64 and 66 until one of the conditions in step 66 is met, at which point flow proceeds to step 68. Steps 68, 70, 72, and 74 check for the end of the ORF in the ascending direction, and perform the same function as steps 60, 62, 64, and 66 but in the opposite direction.

In step 68, M is set to the middle nucleotide. As above for L, this value can be altered in alternative embodiments. In step 70, the sum of the coding states, as above, is compared to T', and M is compared to the length of the nucleic acid sequence. If the sum of the coding states of nucleotide M is greater than or equal to T' and M is less than the length of the nucleic acid sequence, then M is set to M+1 and Q is set to M+1. Flow proceeds to step 72, where, if the sum of the coding states is less than T' and Q is less than the length of the nucleic acid sequence, then Q is set to Q+1. Flow proceeds to step 74, where it is determined if Q−M>T", or Q> length of the nucleic acid sequence. If either is true, then flow proceeds to step 76, where the ORF is determined to extend from nucleotide L to nucleotide M. If in step 74 neither condition is true, then flow loops to step 70.

In an alternative embodiment, different threshold values can be used in place of T' and T" for the second loop, which comprises steps 70, 72, and 74. Different threshold values for steps 62, 64, and 66 versus steps 70, 72, and 74 could be desirable if, for example, one end of an ORF was known or suspected to be degraded to some extent.

Figure 5:
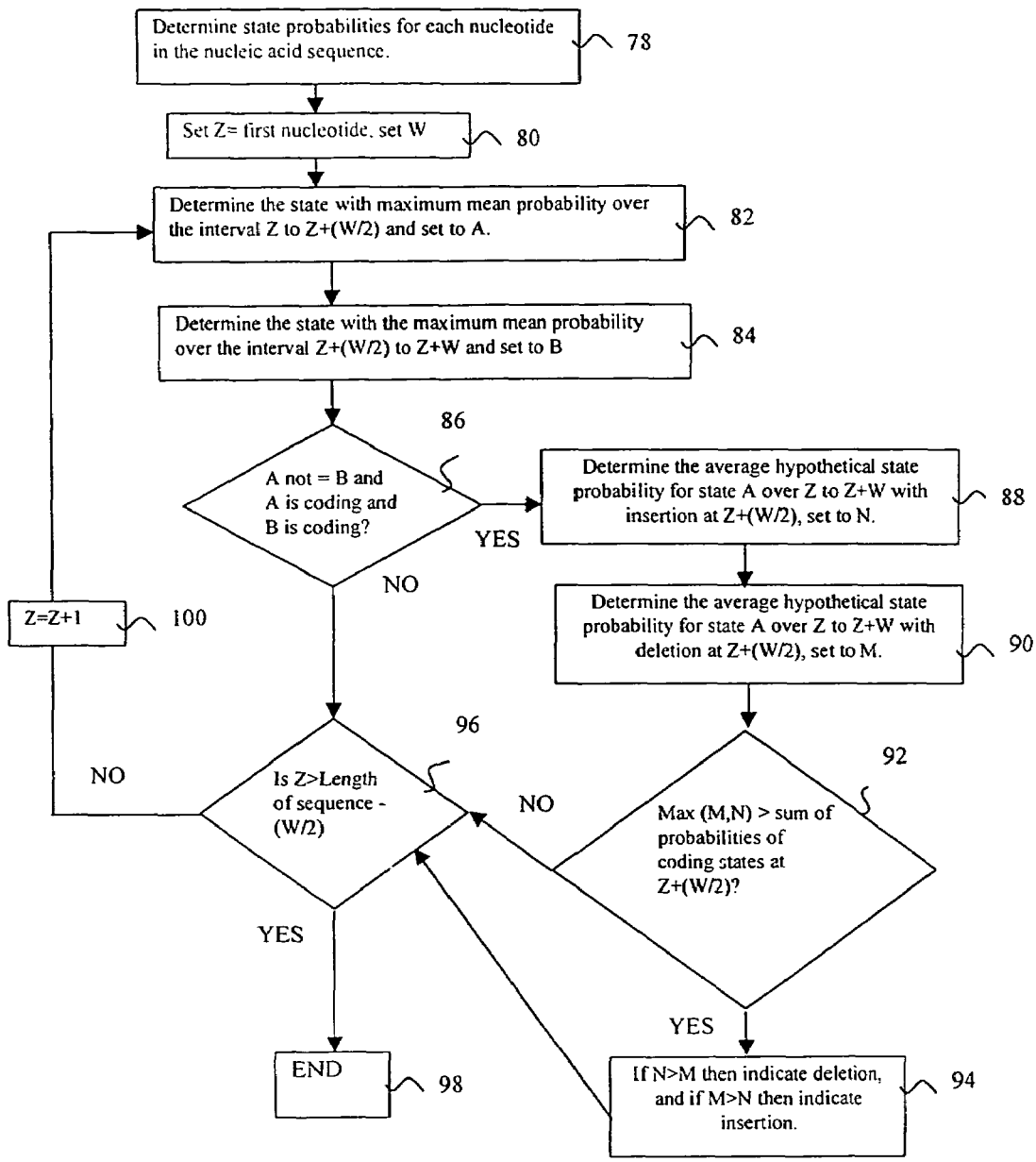
FIG. 5 is a flow chart representing one embodiment of a method for determining the location of insertions and deletions within a nucleic acid sequence.

FIG. 5 is a flowchart representing one embodiment of a method for determining the location of deletions and additions within a nucleic acid sequence. The process first determines the state probabilities for each nucleotide in the nucleic acid sequence. Then the process determines whether in the window around a specific nucleotide the most likely state for the nucleic acid sequence on one side of the specific nucleotide is different from the most likely state for the nucleic acid sequence on the other side of the specific nucleotide. If so, the process determines whether a hypothetical insertion or deletion at the specific nucleotide would sufficiently improve the state probabilities of the entire nucleic acid sequence in the window. If so, then an insertion or a deletion is indicated.

In step 78, the state probabilities of each of the nucleotides in the nucleic acid sequence is determined. As stated above, any probability model that has the correct form of output can be used, with an inhomogeneous Markov model preferred, and the inhomogeneous Markov model described above and represented in FIG. 2 most preferred.

In step 80, the first nucleotide is designated as "Z," and the size of a window, W, is set. In step 82, the probabilities of each of the states of the nucleotides between Z and the midpoint of the window $$Z + \frac{W}{2}$$

are averaged, and the state with the greatest average is set to "A" (windows with an even or odd number of nucleotides are treated as above for the middle nucleotide with respect to determination of $$\frac{W}{2}).$$

"A" is effectively the most likely state of the first half of window W.

In step 84, the probabilities of the states of the nucleotides between the midpoint of the window $$Z + \frac{W}{2}$$

and the end of the window, Z+W, are averaged, and the state with the greatest average is set to B. B is effectively the most likely state of the second half of window W.

In step 86, the most probable states, A and B, are checked to see if they are each a coding state and not the same coding state. If both A and B are coding states and they are not the same coding state, then flow proceeds to steps 88, 90, and 92, where the nucleotide at $$Z + \frac{W}{2}$$

is examined further. If, in step 86, A and B are the same coding state, or if one of the two is most probably a noncoding state, then flow proceeds to 96, where it is determined if Z is greater than the length of the nucleic acid sequence minus $$\frac{W}{2}.$$

If so, then flow proceeds to step 98, and the process ends. If, in step 96, Z is not within a distance of $$\frac{W}{2}$$

of the end of the nucleic acid sequence, then flow proceeds to step 100, where Z is increased by one. Flow then loops to step 82.

If in step 86 if it was determined that both conditions were met, then flow proceeds to steps 88 through 92 to determine if either a deletion or an addition occurred at nucleotide $$Z + \frac{W}{2}.$$

In step 88, a hypothetical average of state probabilities for state A for the entire window, nucleotides Z to Z+W, for an insertion is determined. The hypothetical average of state probabilities for state A is determined for the window as if the nucleotide at $$Z + \frac{W}{2}$$

is removed. The probabilities of state A of the nucleotides in W are averaged to obtain the hypothetical average state probabilities for state A for the entire window, and the value is set to N. In step 90, a hypothetical average of state probabilities for state A for the entire window, nucleotides Z to Z+W, for a deletion is calculated similarly. The hypothetical average of state probabilities for state A in step 90 is determined and set to M for the window as if a nucleotide has been added on one side or the other of the nucleotide at $$Z + \frac{W}{2}.$$

By averaging the state probabilities of all of the nucleotides in the window for either an insertion or a deletion, the values of N and M reflect the likelihood that either an insertion or a deletion has taken place. In steps 88 and 90, in an alternative embodiment, state B can be used in place of state A to achieve a similar result.

In step 92, the larger of M and N is compared to the sum of the probabilities of the states indicating coding (1+, 2+, 3+, 1−, 2−, and 3−) of the nucleotide at $$Z + \frac{W}{2}.$$

If in step 92 neither M nor N is greater than the sum of the probabilities of the coding states of the nucleotide at $$Z = \frac{W}{2},$$

then it is determined that no insertion or deletion has taken place and flow proceeds to step 96. If in step 92 either M or N is greater than the sum of the probabilities of the coding states of the nucleotide at $$Z = \frac{W}{2},$$

then it is determined that an insertion or a deletion has taken place, and flow proceeds to step 94.

In step 94, a deletion is indicated if N is greater than M, and an insertion is indicated if N is not greater than M, and flow then proceeds to step 96.

Figure 6:
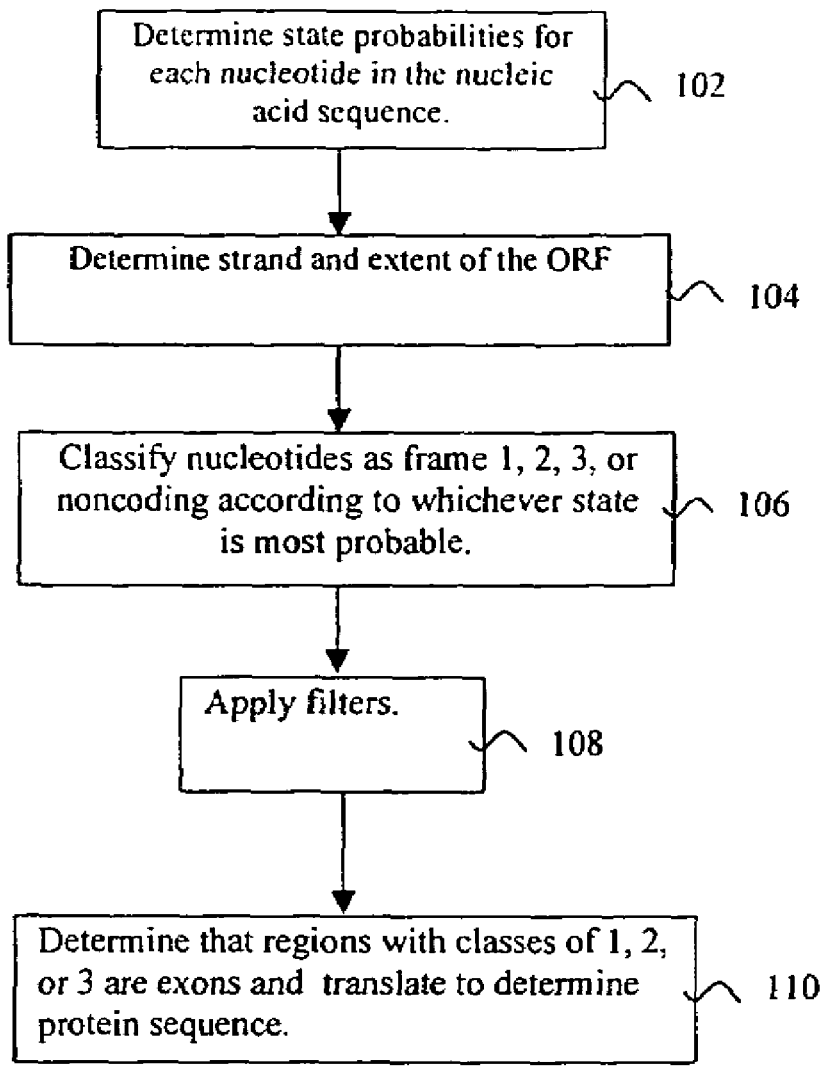
FIG. 6 is a flow chart representing one embodiment of a method for determining the extent of exons within a nucleic acid sequence and the protein translation of those exons.

FIG. 6 is a flow chart representing one embodiment of a method for determining the location of one or more exons within a nucleic acid sequence and the protein translation of those exons. The process begins by determining the state probabilities for each nucleotide in the nucleic acid sequence, the coding strand, and the extent of the open reading frame. The process then classifies each nucleotide according to its most probable state. Filters, which reclassify nucleotides in a defined manner in order to make local blocks of the nucleic acid sequence consistent, are then applied to the nucleic acid sequence. Regions of the nucleic acid sequence that are in any of classes 1, 2, or 3 are then designated as exons, and the exons are translated. Translation is accomplished by using the universal genetic code to convert the nucleic acid sequence of the designated exons into the corresponding amino acid sequence based on the reading frame of the class. That is, exons in class 1 will be translated in reading frame 1, exons in class two will be translated in reading frame 2, and exons in class 3 will be translated in reading frame 3. The translation is linearly arranged to correspond to the linear arrangement of the exons along the nucleic acid sequence.

In step 102, the state probabilities of each of the nucleotides in the nucleic acid sequence are determined. As stated above, any probability model that has the correct form of output can be used, with an inhomogeneous Markov model preferred, and the inhomogeneous Markov model described above and represented in FIG. 2 most preferred. In step 104, the strand and the extent of the open reading frame is determined. Any method for determining the strand and the extent of the ORF that can use the state probabilities generated in step 102 can be used, and in a preferred embodiment, the methods described above and represented in FIGS. 3 and 4 can be used for such determination.

In step 106, the nucleotides in the nucleic acid sequence are categorized as the highest probability state as determined in step 102. For example, in a model having four states for each nucleic acid strand, each nucleotide is categorized as 1, 2, 3, or N.

In step 108, which is optional, one or more filters are applied to the nucleic acid sequence in order to group adjacent nucleotides by class. Any filter that converts portions of the nucleic acid sequence with inconsistent nucleotide classification to a more homogeneous state can be used. The net effect of the application of one or more filters to the nucleic acid sequence classification in step 104 will be to group adjacent nucleotides and blocks of nucleotides into the same coding classification, thereby making exon and introns more uniform, and exon and intron boundaries more evident.

In step 110, the filtered nucleic acid sequence is analyzed for exons. Any contiguous regions with coding classes of 1, 2, or 3 are determined to be exons. Once each exon has been identified, the exons can be translated using the universal genetic code, and a resulting protein sequence derived.

Figure 7:
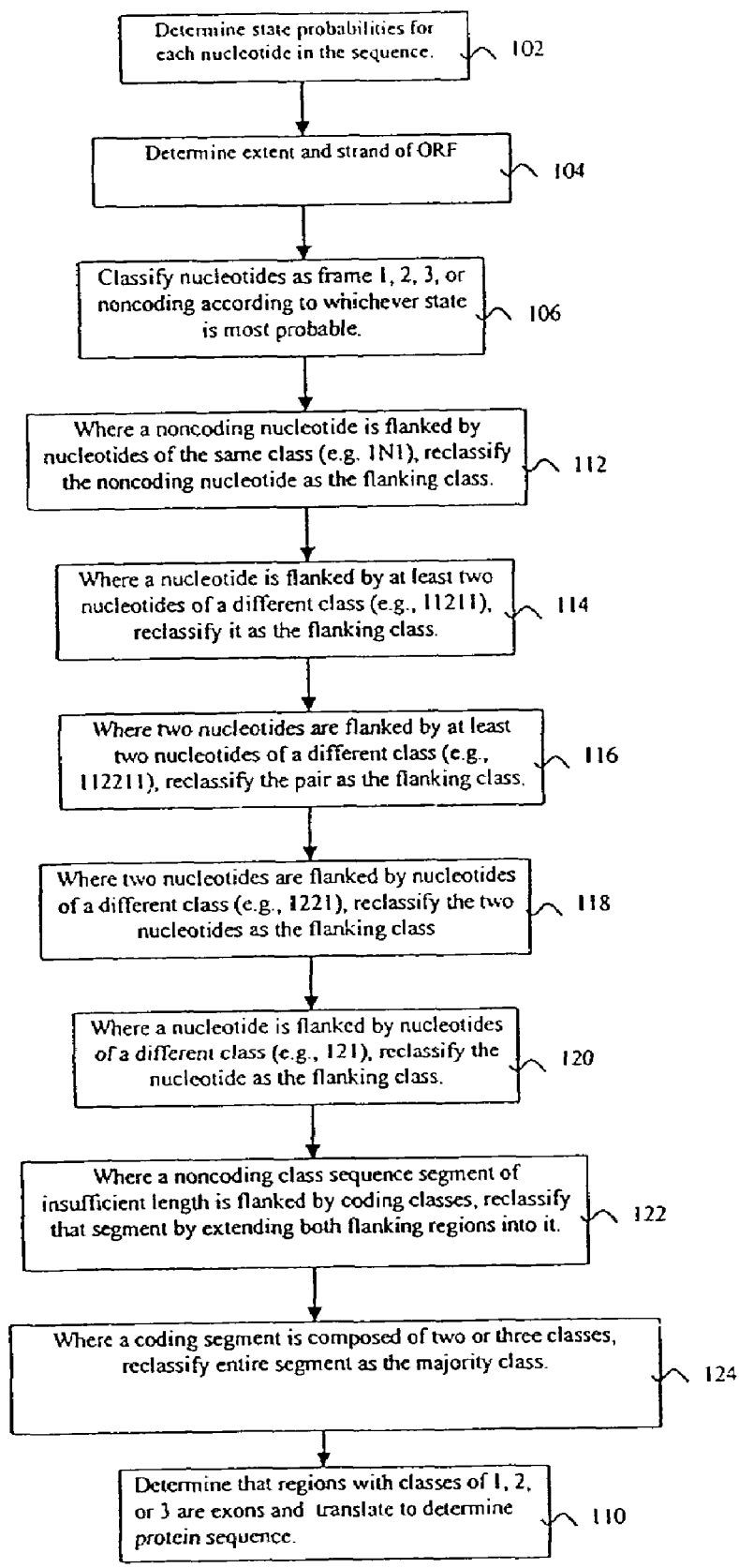
FIG. 7 is a flow chart representing one embodiment of a method for determining the extent of exons within a nucleic acid sequence and the protein translation of those exons.

FIG. 7 is a second embodiment of the method described above and represented in FIG. 6, with explicit filtering steps detailed therein. In FIG. 7, steps 102, 104, 106, and 110 are the same as those described above and shown in FIG. 6. In FIG. 7, after step 106, steps 112, 114, 116, 118, 120, 122, and 124 are filter steps that are applied to the categorized nucleic acid sequence produced in step 106. The order shown for the filter steps, 112, 114, 116, 118, 120, 122, and 124, can be rearranged to occur in any order in the process, and any combination of the steps can be used, including combinations that omit one or more of the filtering steps.

In step 112, any noncoding nucleotide flanked by two nucleotides with the same class is reclassified into the class of the two flanking nucleotides. For example, 1, N,1 would be converted to 1,1,1.

In step 114, any nucleotide that is flanked by two pairs of adjacent nucleotides all with the same class is reclassified into the class of the flanking nucleotides. For example, 1,1,2,1,1 would be converted to 1,1,1,1,1.

In step 116, any adjacent nucleotide pair having the same class that is flanked by two pairs of adjacent nucleotides all with the same class is reclassified into the class of the flanking nucleotides. For example, 1,1,2,2,1,1 would be converted to 1,1,1,1,1,1.

In step 118, any adjacent nucleotide pair having the same class that is flanked by two nucleotides with the same class is reclassified into the class of the flanking nucleotides. For example, 1,2,2,1 would be converted to 1,1,1,1.

In step 120, any nucleotide flanked by two nucleotides with the same class is reclassified into the class of the flanking nucleotides. For example, 1,2,1 is converted to 1,1,1.

In step 122, any contiguous, noncoding nucleotide region with an insufficient length is reclassified into the class of the flanking coding regions. An insufficient length is any length that is too small to be an intron. This length will be dependent in large part upon the particular nucleic acid sequence under study. In one embodiment, a length of about 10 to 50, preferably about 20 to 40, and more preferably about 25 to 35 nucleotides in length is used. The size of the noncoding nucleotide length required can, in alternative embodiments, be changed as appropriate to better suit examination of the nucleic acid sequence under study. In step 122, the classification of the flanking regions of coding nucleotides can be extended into the noncoding regions an equal amount on either side, an unequal amount on either side, or entirely on one side or the other.

In step 124, any coding region (i.e. a region with nucleotides of classes 1, 2, or 3, comprising more than one nucleotide classification) is reclassified as the most common class in that coding segment.

Flow proceeds to step 110, where the filtered nucleic acid sequence is analyzed for exons. Any contiguous regions with nucleotides of classes 1, 2, or 3 are determined to be exons. Once each exon has been identified, the exons can be translated using the universal genetic code, and a resulting protein sequence derived.

Figure 8A:
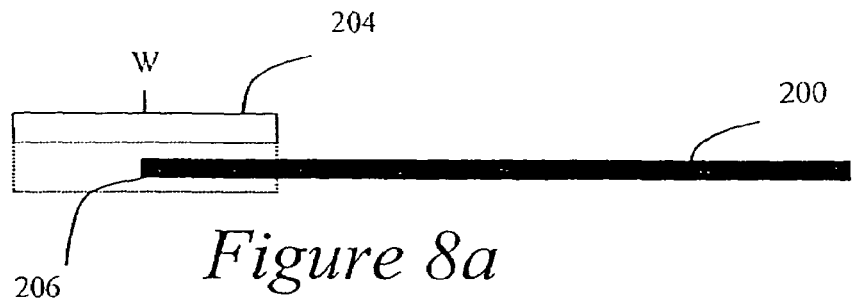
FIG. 8a is a schematic representation of a window located at the end of a nucleic acid sequence.

While performing the methods described above in FIGS. 1-7, windows can sometimes extend past the end of a sequence. Conventional applications that use window-based probability models for multiple nucleotides, such as the windows described above, are limited in their application at the ends of nucleic acid sequences. Since coding probability can be calculated using a window that is centered on each nucleotide of a nucleic acid sequence in turn, a window can extend beyond an end of a sequence. FIG. 8a schematically represents a nucleic acid sequence 200 with a window 204 of length "W." As shown in FIG. 8a, the window 204 is empty for the first $$\frac{W}{2}$$

bases at an end 206 of the sequence 200.

Figure 8B:
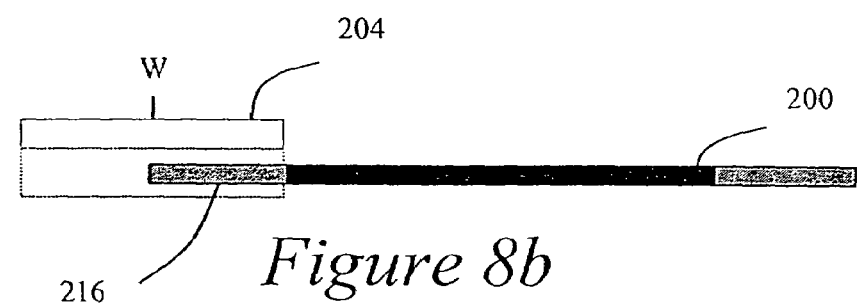
FIG. 8b is a schematic representation of a window located at the end of a nucleic acid sequence showing nucleotides near the end of the nucleic acid sequence.
Figure 8C:
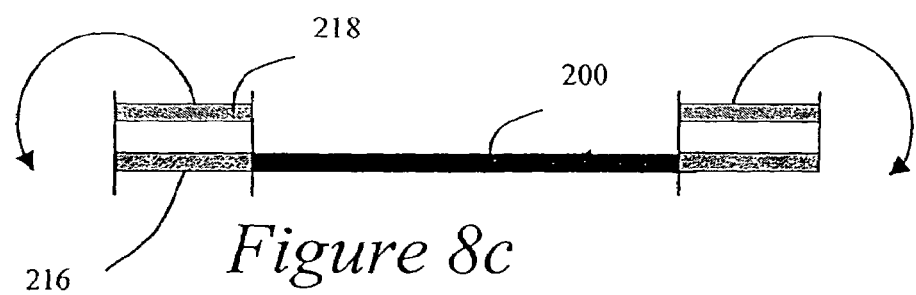
FIG. 8c is a schematic representation showing the ends of a nucleic acid sequence being copied to form a hypothetical extension on each end of the nucleic acid sequence.
Figure 8D:
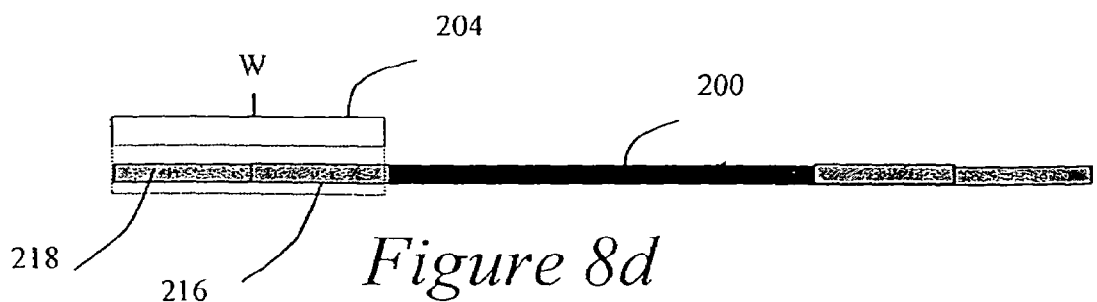
FIG. 8d is a schematic representation of a nucleic acid sequence showing the appended hypothetical extensions.

As shown in FIG. 8b, the present invention remedies this problem by using the local nucleic acid sequence 216 at the end 206 of the nucleic acid sequence 200 as a source for hypothetical nucleotides added on to the end 206 the nucleic acid sequence 206. As shown in FIG. 8c, a copy 218 of the local nucleic acid sequence 216 can be created. As shown in FIG. 8d, the copy 218 can then be appended onto the end 206 to form a hypothetical nucleic acid sequence extension. As shown in FIG. 8d, the window 204 is now filled with nucleotides from the nucleic acid sequence 200 and the hypothetical nucleic acid sequence extension 218, which allows for probability determination within the window 204. As shown in FIGS. 8b, 8c, and 8d, the same process can be performed on the other end of the sequence at the same time. Any number of nucleotides can be copied and added in this manner in order to provide the correct size window. In a preferred embodiment, the number of nucleotides copied is a multiple of three. For example, if a 100 nucleotide window is desired for the first nucleotide in the nucleic acid sequence, the first 51 nucleotides of the nucleic acid sequence can be copied to form a hypothetical 51 nucleotide extension. When state probabilities are determined for the first nucleotide, the 51 appended nucleotides are used to fill the first half of the window. The same or different nucleotides can be copied and used in a similar manner for any other nucleotides without a sufficient window. This process can be repeated for the other end of the nucleic acid sequence, of course, as needed. The copied nucleotides can be appended in either orientation on the end of the nucleic acid sequence.

Figure 9A:
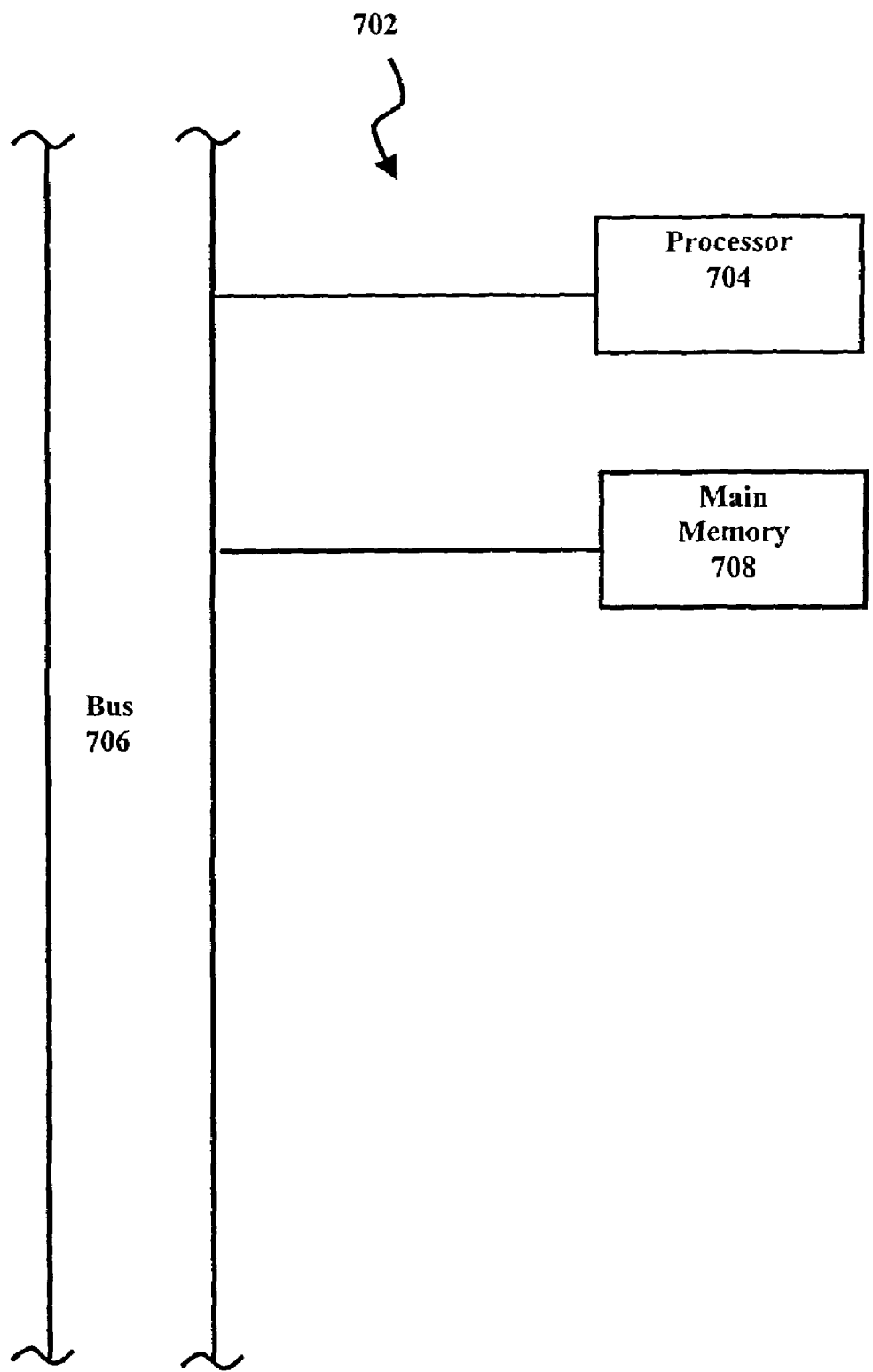
FIG. 9a is a schematic representation of one embodiment of a computer system that can implement the methods of the present invention.

Implementation:

A computer system capable of carrying out the functionality and methods described above is shown in more detail in FIG. 9a. A computer system 702 includes one or more processors, such as a processor 704. The processor 704 is connected to a communication bus 706. The computer system 702 also includes a main memory 708, which is preferably random access memory (RAM). Various software embodiments are described in terms of this exemplary computer system. After reading this description, it will become apparent to a person skilled in the relevant art how to implement the invention using other computer systems and/or computer architectures.

Figure 9B:
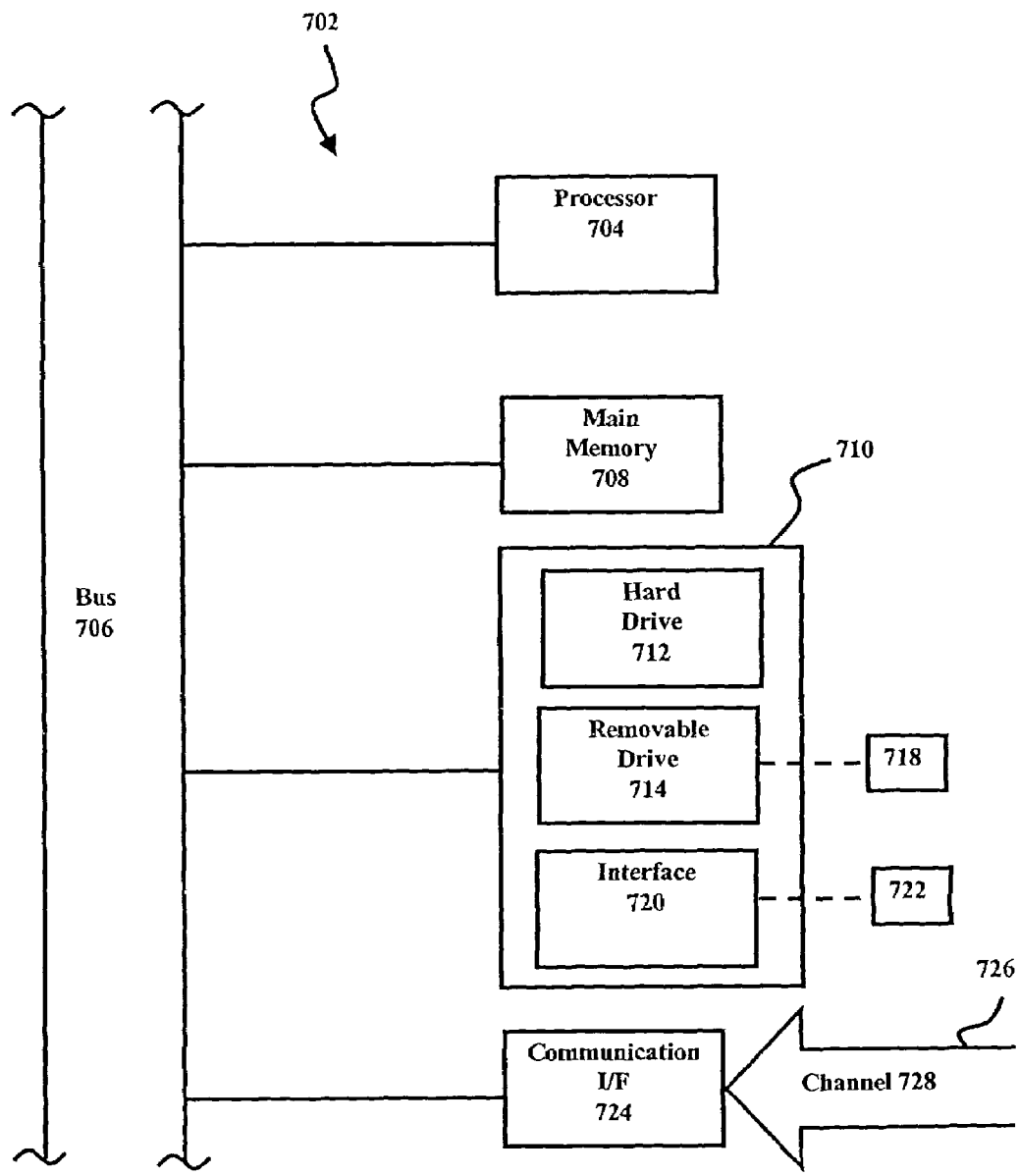
FIG. 9b is a schematic representation of one embodiment of a computer system that can implement the methods of the present invention.

In a further embodiment, shown in FIG. 9b, the computer system can also include a secondary memory 710. The secondary memory 710 can include, for example, a hard disk drive 712 and/or a removable storage drive 714, representing a floppy disk drive, a magnetic tape drive, or an optical disk drive, among others. The removable storage drive 714 reads from and/or writes to a removable storage unit 718 in a well known manner. The removable storage unit 718, represents, for example, a floppy disk, magnetic tape, or an optical disk, which is read by and written to by the removable storage drive 714. As will be appreciated, the removable storage unit 718 includes a computer usable storage medium having stored therein computer software and/or data.

In alternative embodiments, the secondary memory 710 may include other similar means for allowing computer programs or other instructions to be loaded into the computer system. Such means can include, for example, a removable storage unit 722 and an interface 720. Examples of such can include a program cartridge and cartridge interface (such as that found in video game devices), a removable memory chip (such as an EPROM, or PROM) and associated socket, and other removable storage units 722 and interfaces 720 which allow software and data to be transferred from the removable storage unit 722 to the computer system.

The computer system can also include a communications interface 724. The communications interface 724 allows software and data to be transferred between the computer system and external devices. Examples of the communications interface 724 can include a modem, a network interface (such as an Ethernet card), a communications port, a PCMCIA slot and card, etc. Software and data transferred via the communications interface 724 are in the form of signals 726 that can be electronic, electromagnetic, optical or other signals capable of being received by the communications interface 724. Signals 726 are provided to communications interface via a channel 728. A channel 728 carries signals 726 in two directions and can be implemented using wire or cable, fiber optics, a phone line, a cellular phone link, an RF link and other communications channels. In one embodiment, the channel is a connection to a network The network can be any network known in the art, including, but not limited to, LANs, WANs, and the Internet. Nucleic acid sequence data can be stored in remote systems, databases, or distributed databases, among others, for example GenBank, and transferred to computer system for processing via the network. In a preferred embodiment, nucleic acid sequence data is received through the Internet via the channel 728. Nucleic acid sequences can be input into the system and stored in the main memory 708. Input devices include the communication and storage devices described herein, as well as keyboards, voice input, and other devices for transferring data to a computer system. In a further embodiment, nucleic acid sequences can be generated by an automatic sequencer, for example any that are known in the art, and the implementations described herein can be incorporated within the automatic sequencer device in order to directly use the output of the automatic sequencer.

In this document, the terms "computer program medium" and "computer usable medium" are used to generally refer to media such as the removable storage device 718, a hard disk installed in hard disk drive 712, and signals 726. These computer program products are means for providing software to the computer system.

Computer programs (also called computer control logic) are stored in the main memory 708 and/or the secondary memory 710. Computer programs can also be received via the communications interface 724. Such computer programs, when executed, enable the computer system to perform the features of the present invention as discussed herein. In particular, the computer programs, when executed, enable the processor 704 to perform the features of the present invention. Accordingly, such computer programs represent controllers of the computer system.

In an embodiment where the invention is implemented using software, the software may be stored in a computer program product and loaded into the computer system using the removable storage drive 714, the hard drive 712 or the communications interface 724. The control logic (software), when executed by the processor 704, causes the processor 704 to perform the functions of the invention as described herein.

In another embodiment, the invention is implemented primarily in hardware using, for example, hardware components such as application specific integrated circuits (ASICs). In one embodient incorporating ASIC technology, a self-contained device, which could be hand-held, has integrated circuits specific to perform the methods described above without the need for software. Implementation of such a hardware state machine so as to perform the functions described herein will be apparent to persons skilled in the relevant art(s). In yet another embodiment, the invention is implemented using a combination of both hardware and software.

The following examples are illustrative only. It is not intended that the present invention be limited to the illustrative embodiments.

EXAMPLE 1

Figure 10A:
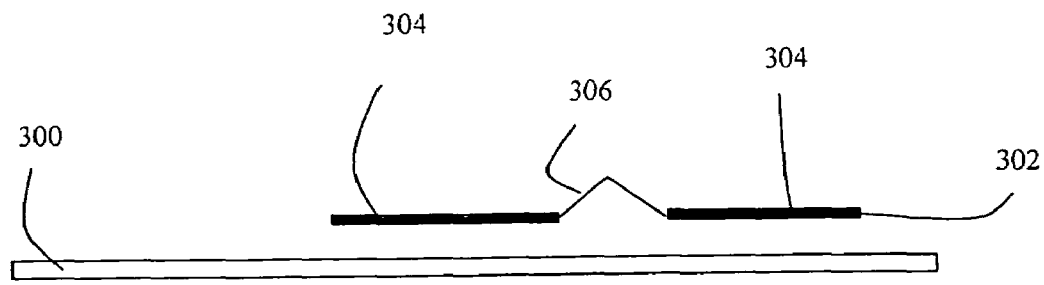
FIG. 10a is a schematic representation of a genomic sequence of DNA with an aligned expressed sequence tag aligned thereto.
Figure 10B:
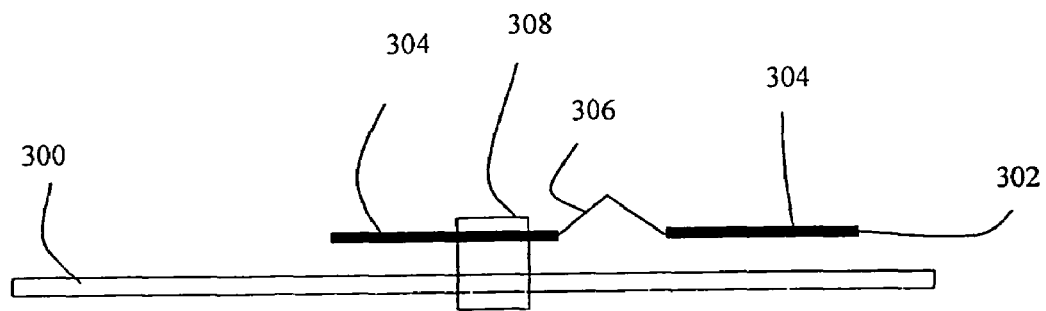
FIG. 10b is a schematic representation of a window in a region of DNA when the entire region is in a known coding region; and, FIG. 10c is a schematic representation of a window in a region of DNA when part of the region is known to be coding, and part of the region is known to be noncoding.
Figure 10C:
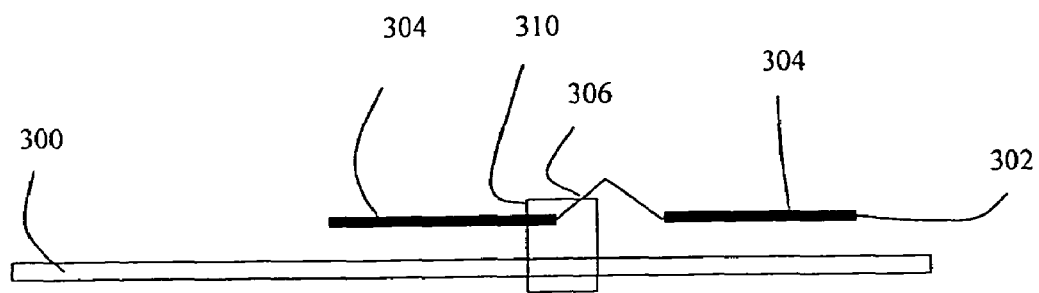

Referring now to FIGS. 10a, 10b, and 10c, examples of biasing are shown. FIG. 10a shows a portion of genomic DNA 300. Aligned with the genomic DNA 300 is an expressed sequence tag (EST) 302. The EST 302 comprises coding regions 304 and noncoding regions 306. In FIG. 10b a window 308 of nucleotides is examined. The window 308 is positioned on the genomic DNA 300 that corresponds to a known coding region 304 on the EST 302. The a priori probability of coding is said to be 100% over that window 308 and a bias is applied accordingly. In FIG. 10c, a different window 310 straddles the intron-exon boundary, and the a priori probability of coding is said to be 100% for the nucleotides in the window 310 that correspond to the coding region 304 of the EST 302, while the a priori probability of coding is said to be 0% for the nucleotides in the window 310 that correspond to the noncoding region 306 of the EST 302.

Bias is applied to the two different situations shown in FIGS. 10b and 10c as follows. The general equation for the probability of the sequence $S=a_1 \ldots a_w$ of a Markov process of order n is shown in Equation VII:

$$P(a_1 \ldots a_w) = P(a_1 \ldots a_n) \cdot P(a_{n+1}|a_1 \ldots a_n) \cdot \ldots P(a_w|a_{w-n} \ldots a_{w-1}) \quad \text{(VII)}$$

This equation is based on an inhomogeneous Markov model, whereby the initial and transitional probabilities are dependent on the periodic state of the sequence (as in a hidden Markov model with fixed state transition probabilities). In this model, initial and transition probabilities are dependent on the sequence orientation and phase in which the sequence is read relative to the codons in the coding portion of the nucleic acid sequence. Thus, equation VIII is used:

$$P_f(S) = P_f(a_1 \ldots a_n) \cdot \prod_{i=1}^{\omega-n} P_{F(i,\sigma)}(a_{n+i}|a_i \ldots a_{n+i-1}) \quad \text{(VIII)}$$

where, given a state $\sigma \in \{1+, 2+, 3+, N+, 1-, 2-, 3-, N-\}$ representing the possible states for reading the sequence, wherein . . .

$$F(i) = \begin{cases} i \bmod 3 + 1 & \text{if } f = 1\pm \\ (i+1) \bmod 3 + 1 & \text{if } f = 2\pm \\ (i+2) \bmod 3 + 1 & \text{if } f = 3\pm \\ N & \text{if } f = N\pm \end{cases} \quad \text{(IX)}$$

Equation X is used to apply Bayes' rule to determine the probability that the sequence S is in state σ:

$$P(\sigma|S) = \frac{P_\sigma \cdot P_\sigma(S)}{\sum_{i \in \{1+,2+,3+,N+,1-,2-,3-,N-\}} P_i \cdot P_i(S)} \quad \text{(X)}$$

A bias function is added to equation X in order to allow for biasing of regions of DNA for which coding information is available. The bias function is incorporated in equation XI:

$$P(\sigma|S) = \frac{\phi(\sigma) \cdot P_\sigma \cdot P_\sigma(S)}{\sum_{i \in \{1^+,2^+,3^+,N^+,1^-,2^-,3^-,N^-\}} \phi(\sigma) \cdot P_i \cdot P_i(S)} \quad (XI)$$

Equation XI can be applied to the hypothetical region of DNA shown in the window 308 in FIG. 10*b*. Since the entirety of the sequence in the window 308 lies in a coding region (as determined with the EST 302), a bias function $\phi(\sigma)$ can be defined according to equation XII:

$$P(\sigma|S) = \begin{cases} 1 & \text{if } \sigma \in \{1^+, 2^+, 3^+\} \\ 0 & \text{if } \sigma \in \{1^-, 2^-, 3^-, N^+, N^-\} \end{cases} \quad (XII)$$

which reflects that we know with 100% certainty that the sequence segment must be coding in one of the thee direct reading frames, but that we do not know which. In this case, since $\phi(\sigma)=0$ where $\sigma \in \{N+, 1-, 2-, 3-, N-\}$, equation XII can be written as equation. XIII:

$$P(\sigma|S) = \begin{cases} 0 & \text{if } \sigma \in \{1^-, 2^-, 3^-, N^+, N^-\} \\ P_\sigma \cdot P_\sigma(S) \cdot \left[ \sum_{i \in \{1^+,2^+,3^+\}} P_i \cdot P_i(S) \right]^{-1} & \text{if } \sigma \in \{1^+, 2^+, 3^+\} \end{cases} \quad (XIII)$$

Because $P_{1+}=P_{2+}=P_{3+}$ (since the EST does not indicate any difference in probability among the three reading frames), equation XIII can be simplified as shown in equation XIV:

$$P(\sigma|S) = \begin{cases} 0 & \text{if } \sigma \in \{1^-, 2^-, 3^-, N^+, N^-\} \\ P_\sigma(S) \cdot \left[ \sum_{i \in \{1^+,2^+,3^+\}} P_i(S) \right]^{-1} & \text{if } \sigma \in \{1^+, 2^+, 3^+\} \end{cases} \quad (XIV)$$

The function $\phi(\sigma)$ results in a coding potential (equation XIV) substantially different than the unbiased coding potential function (shown by equation X). In this example, the chosen bias function reduces the probability of the evaluated window 308 to zero in all but the three plus-strand coding states. This effectively forces the window to be evaluated as coding in one of the positive coding states, while not biasing the probability of those states relative to each other (e.g., $$\frac{P_{1+}}{P_{2+}}$$

is the same with or without the bias function whereas $$\frac{P_{1-}}{P_{1+}}$$

may differ).

FIG. 10*c* illustrates a window 310 wherein the evaluated sequence straddles an exon-intron boundary as indicated by the EST 302. A possible function $\phi(\sigma)$ for this situation would be to expand equation XII to equation XIII:

$$P(\sigma|S) = \begin{cases} e & \text{if } \sigma \in \{1^+, 2^+, 3^+\} \\ 1-e & \text{if } \sigma \in \{N^+, N^-\} \\ 0 & \text{if } \sigma \in \{1^-, 2^-, 3^-\} \end{cases} \quad (XIII)$$

where e represents the fraction of bases in the part of the sequence in the window that lies in the coding region of the DNA 300 as indicated by the coding region 304 of the EST 302. If equation XIII is put into equation IX, equation XIV results:

$$P(\sigma|S) = \begin{cases} 0 & \text{if } \sigma \in \{1^-, 2^-, 3^-\} \\ e \cdot P_\sigma \cdot P_\sigma(S) \cdot \left[ \sum_{i \in \{1^+,2^+,3^+,N^+,N^-\}} \phi(i) \cdot P_\sigma \cdot P_i(S) \right]^{-1} & \text{if } \sigma \in \{1^+, 2^+, 3^+\} \\ (1-e) \cdot P_\sigma \cdot P_\sigma(S) \cdot \left[ \sum_{i \in \{1^+,2^+,3^+,N^+,N^-\}} \phi(i) \cdot P_\sigma \cdot P_i(S) \right]^{-1} & \text{if } \sigma \in \{N^+, N^-\} \end{cases} \quad (XIV)$$

where $$P_\sigma = \frac{1}{4}$$

for $\sigma \in \{N+, N-\}$ and $$\frac{1}{6}$$

for $\sigma \in \{1+, 2+, 3+\}$ (given the assumption that coding and noncoding are equiprobable events, each coding state is equiprobable with any other coding state, and that both non-coding states are equiprobable, $$\frac{1}{4} \times 2 = \frac{1}{2} \text{ and } \frac{1}{6} \times 3 = \frac{1}{2} \bigg).$$

EXAMPLE 2

The following example illustrates the computations involved in probability calculations for a sequence with and without a bias applied. The nucleotide sequence GATGACATT is used in this example for clarity and simplicity, but it is understood that longer sequences as indicated above can be used. Further, for this example, a zero order inhomogeneous Markov model is used. In this model, the initial probabilities are all 1 and each event is independent of that which precedes it ($a_1 \ldots a_k \rightarrow a_{k+1}$ becomes $N \rightarrow a_1$ because k is zero). Models of higher order can be used, as described above.

Accordingly, the following hypothetical table of probabilities is used:

|   | Direct (+) | | | Reverse (−) | | | |
|---|---|---|---|---|---|---|---|
|   | 1+ | 2+ | 3+ | 1− | 2− | 3− | N± |
| T | 0.13 | 0.27 | 0.13 | 0.10 | 0.25 | 0.21 | 0.20 |
| C | 0.28 | 0.26 | 0.39 | 0.39 | 0.21 | 0.38 | 0.30 |
| A | 0.21 | 0.26 | 0.09 | 0.13 | 0.27 | 0.13 | 0.21 |
| G | 0.38 | 0.21 | 0.39 | 0.38 | 0.26 | 0.28 | 0.29 |

Without a bias function $\emptyset(\sigma)$ to incorporate known information in the calculations, $P(S|\sigma)$ can be calculated for the zero order case for the sequence GATGACATT according to equations XV through XXI.

$$P(GATGACATT|1^+) = P(N) \cdot P_{1+}(G|N) \cdot P_{2+}(A|N) \cdot P_{3+}(T|N) \cdot \\ P_{1+}(G|N) \cdot P_{2+}(A|N) \cdot P_{3+}(C|N) \cdot \\ P_{1+}(A|N) \cdot P_{2+}(T|N) \cdot P_{3+}(T|N) \\ = P_{1+}(G) \cdot P_{2+}(A) \cdot P_{3+}(T) \cdot \\ P_{1+}(G) \cdot P_{2+}(A) \cdot P_{3+}(C) \cdot \\ P_{1+}(A) \cdot P_{2+}(T) \cdot P_{3+}(T) \\ = 0.38 \times 0.26 \times 0.13 \times 0.38 \times 0.26 \times \\ 0.39 \times 0.21 \times 0.27 \times 0.13 \\ = 3.6479448 \times 10^{-6}$$
(XV)

$$P(GATGACATT|2^+) = P_{2+}(G) \cdot P_{3+}(A) \cdot P_{1+}(T) \cdot \\ P_{2+}(G) \cdot P_{3+}(A) \cdot P_{1+}(C) \cdot \\ P_{2+}(A) \cdot P_{3+}(T) \cdot P_{1+}(T) \\ = 0.21 \times 0.09 \times 0.13 \times 0.21 \times 0.09 \times \\ 0.28 \times 0.26 \times 0.13 \times 0.13 \\ = 5.71332739 \times 10^{-8}$$
(XVI)

$$P(GATGACATT|3^+) = P_{3+}(G) \cdot P_{1+}(A) \cdot P_{2+}(T) \cdot \\ P_{3+}(G) \cdot P_{1+}(A) \cdot P_{2+}(C) \cdot \\ P_{3+}(A) \cdot P_{1+}(T) \cdot P_{2+}(T) \\ = 0.39 \times 0.21 \times 0.27 \times 0.39 \times 0.21 \times \\ 0.26 \times 0.09 \times 0.13 \times 0.27 \\ = 1.4874917 \times 10^{-6}$$
(XVII)

$$P(GATGACATT|1^-) = P_{1-}(G) \cdot P_{2-}(A) \cdot P_{3-}(T) \cdot \\ P_{1-}(G) \cdot P_{2-}(A) \cdot P_{3-}(C) \cdot \\ P_{1-}(A) \cdot P_{2-}(T) \cdot P_{3-}(T) \\ = 0.38 \times 0.27 \times 0.21 \times 0.38 \times 0.27 \times \\ 0.38 \times 0.13 \times 0.25 \times 0.21 \\ = 5.7332419 \times 10^{-6}$$
(XVIII)

$$P(GATGACATT|2^-) = P_{2-}(G) \cdot P_{3-}(A) \cdot P_{1-}(T) \cdot \\ P_{2-}(G) \cdot P_{3-}(A) \cdot P_{1-}(C) \cdot \\ P_{2-}(A) \cdot P_{3-}(T) \cdot P_{1-}(T) \\ = 0.26 \times 0.13 \times 0.10 \times 0.26 \times 0.13 \times \\ 0.39 \times 0.27 \times 0.21 \times 0.10 \\ = 2.5262776 \times 10^{-7}$$
(XIX)

$$P(GATGACATT|3^-) = P_{3-}(G) \cdot P_{1-}(A) \cdot P_{2-}(T) \cdot \\ P_{3-}(G) \cdot P_{1-}(A) \cdot P_{2-}(C) \cdot \\ P_{3-}(A) \cdot P_{1-}(T) \cdot P_{2-}(T) \\ = 0.28 \times 0.13 \times 0.25 \times 0.28 \times 0.13 \times \\ 0.21 \times 0.13 \times 0.10 \times 0.25 \\ = 2.2607130 \times 10^{-7}$$
(XX)

$$P(GATGACATT|N) = P_N(G) \cdot P_N(A) \cdot P_N(T) \cdot \\ P_N(G) \cdot P_N(A) \cdot P_N(C) \cdot \\ P_N(A) \cdot P_N(T) \cdot P_N(T) \\ = 0.29 \times 0.21 \times 0.20 \times 0.29 \times 0.21 \times \\ 0.30 \times 0.21 \times 0.20 \times 0.20 \\ = 1.8692402 \times 10^{-6}$$
(XXI)

Given the values of $P(S|\sigma)$, we can determine the probability that the given sequence segment is in state $\sigma$, $P(\sigma|S)$ using equation XXII (Bayes' Rules):

$$P(\sigma|S) = \frac{P(\sigma) \cdot P(S|\sigma)}{\sum_i [P(i) \cdot P(S|i)]}$$
(XXII)

Equations XXIII through XXIX show the calculations for each of the states.

$$P(1^+|S) = \frac{P(1^+) \cdot P(S|1^+)}{\sum_i [P(i) \cdot P(S|i)]} \\ = \frac{\frac{1}{12}(3.6479448 \times 10^{-6})}{\frac{1}{2}(3.6479448 \times 10^{-6}) + \ldots + \frac{1}{2}(1.8692402 \times 10^{-6})} \\ = \frac{3.0399540 \times 10^{-7}}{1.1060761 \times 10^{-6}} \\ = 0.27484131$$
(XXIII)

$$P(2^+|S) = \frac{4.7611061 \times 10^{-9}}{1.1060761 \times 10^{-6}} \\ = 0.004304501$$
(XXIV)

$$P(3^+|S) = \frac{1.12395764 \times 10^{-7}}{1.1060761 \times 10^{-6}} \\ = 0.11156173$$
(XXV)

$$P(1^-|S) = \frac{4.7777016 \times 10^{-7}}{1.1060761 \times 10^{-6}} \\ = 0.43195053$$
(XXVI)

$$P(2^-|S) = \frac{2.1052313 \times 10^{-8}}{1.1060761 \times 10^{-6}} \\ = 0.019033331$$
(XXVII)

$$P(3^-|S) = \frac{1.8839275 \times 10^{-8}}{1.1060761 \times 10^{-6}} = 0.017032531 \quad \text{(XXVIII)}$$

$$P(N|S) = \frac{1.557002 \times 10^{-7}}{1.1060761 \times 10^{-6}} = 0.14076807 \quad \text{(XXIX)}$$

The coding probability function indicates a 43% probability that the sequence is coding in the first reading frame of the reverse-complement strand (−) of the sequence provided, based on the zero order inhomogeneous Markov model used. While the most probable state, it is also true that there is a greater probability (57%) that the sequence is not in that state.

An investigator can apply the bias function method to impose a bias based on prior knowledge of sequence features, such as an EST alignment to the subject sequence, or homology to a previously characterized sequence. For example, given an EST alignment to the subject sequence that implies the sequence is coding on the positive strand, a bias function can be defined that summarizes that observation. Equation XXX is one example of such a function:

$$\phi(\sigma) = \begin{cases} 0.95 & \text{if } \sigma \in \{1^+, 2^+, 3^+\} \\ 0.05 & \text{if } \sigma \notin \{1^+, 2^+, 3^+\} \end{cases} \quad \text{(XXX)}$$

This bias function does not exclude the possibility that the sequence is noncoding or coding on the reverse complement strand, although it does effectively bias the a priori probability that the sequence is coding in one of the forward three reading frames. The function above states that the three forward coding states are 19-fold (0.95/0.05) more probable than the other states, which is an assertion by the investigator that he is confident that the EST alignment is correct in indicating that the sequence is coding on that strand.

Given the bias function defined above, the values for $P'(S|\sigma)$ are determined as before for the unbiased case. To calculate $P'(\sigma|S)$, however, equation XXXI is used:

$$P'(\sigma|S) = \frac{\phi(\sigma) \cdot P(\sigma) \cdot P(S|\sigma)}{\sum_i [\phi(i) \cdot P(i) \cdot P(S|i)]} \quad \text{(XXXI)}$$

The equations to determine $P'(\sigma|S)$ for each state are shown in equations XXXII through XXXVIII:

$$P'(1^+|S) = \frac{\phi(1^+) \cdot P(1^+) \cdot P(S|1^+)}{\sum_i [\phi(i) \cdot P(i) \cdot P(S|i)]} \quad \text{(XXXII)}$$

$$= \frac{0.95 \cdot \frac{1}{12}(3.6479448 \times 10^{-6})}{0.95 \cdot \frac{1}{12}(3.6479448 \times 10^{-0}) + \ldots + 0.05 \cdot \frac{1}{2}(1.8692402 \times 10^{-6})}$$

$$= \frac{2.8879563 \times 10^{-7}}{4.4399294 \times 10^{-7}} = 0.65045095$$

$$P'(2^+|S) = 0.95 \frac{\frac{1}{12} \cdot P(S|2^+)}{4.4399294 \times 10^{-7}} = 0.010187213 \quad \text{(XXXIII)}$$

$$P'(3^+|S) = 0.95 \frac{\frac{1}{12} \cdot P(S|3^+)}{4.4399294 \times 10^{-7}} = 0.2652289 \quad \text{(XXXIV)}$$

$$P'(1^-|S) = 0.05 \frac{\frac{1}{12} \cdot P(S|1^-)}{4.4399294 \times 10^{-7}} = 0.05380379 \quad \text{(XXXV)}$$

$$P'(2^-|S) = 0.05 \frac{\frac{1}{12} \cdot P(S|2^-)}{4.4399294 \times 10^{-7}} = 0.0023707938 \quad \text{(XXXVI)}$$

$$P'(3^-|S) = 0.05 \frac{\frac{1}{12} \cdot P(S|3^-)}{4.4399294 \times 10^{-7}} = 0.00042392676 \quad \text{(XXXVII)}$$

$$P'(N|S) = 0.05 \frac{\frac{1}{2} \cdot P(S|N)}{4.4399294 \times 10^{-7}} = 0.0017534085 \quad \text{(XXXVIII)}$$

Given the bias function $\phi(\sigma)$, the resulting coding potential calculation indicates a 65% probability that the sequence is coding in the first reading frame on the forward strand. The result represents the coding probability given the assumptions of the investigator stated as the bias function.

EXAMPLE 3

The following is a copy of the output of a program implementing the method described above with and without a bias function. The following sequence is a genomic sample from the organism *Arabidopsis thaliana, landsberg*.

```
TACTCAAAAATATATTCCATGCTTAATTAGGCCGGATTCGCGGTGACGATGCACCAAGAGCGGTTTTTCCGA    (SEQ. ID. NO. 1)
GCATTGTAGGCCGTCCTCGCCACACCGGTGTGATGGTTGGGATGGGACAAAAGGATGCTTATGTTGGAGACGAGGCTC
AATCAAAACGTGGTATCTTGACTCTGAAGTACCCAATTGAGCATGGAATTGTTAATAATTGGGATGACATGGAGAAGA
TTTGGCATCACACTTTCTACAATGAGCTTCGTGTTGCCCCTGAAGAACATCCGGTTCTCTTGACCGAAGCTCCTCTCA
ATCCGAAAGCTAACCGTGAGAAGATGACTCAGATCATGTTTGAGACATTCAATACTCCTGCTATGTATGTTGCCATTC
AAGCTGTTCTCTCACTCTATGCCAGTGGCCGTACTACTGGTCAGTACATTACTACATTCTTTTTATACCGTTTGGTTG
```

-continued

```
AAATAAAATTCGGTTTGGTTCGATTCGAGTTTGCTCTCATTATTTTTATTTTGTTGGTTAGGTATTGTTTTGGACTCC
GGAGATGGTGTGAGCCACACGGTACCAATCTACGAGGGTTATGCACTTCCACACGCAATCCTGCGTCTTGATCTTGCA
GGTCGTGACCTAACCGACCACCTTATGAAAATCCTGACAGAGCGTGGTTACTCTTTCACCACAACTGCTGAGCGTGAG
ATTGTTAGAGACATGAAGGAGAAGCTCTCTTACATTGCCTTGGACTTTGAACAAGAGCTCGAGACTTCCAAAACAAGC
TCATCCGTTGAGAAGAGCTTCGAGCTGCCAGACGGTCAAGTGATCACCATCGGGGCAGAGCGTTTCCGATGCCCTGAA
GTTCTGTTTCAGCCATCGATGATCGGAATGGAAAATCCGGGAATTCATGAAACTACTTACAACTCAATCATGAAATGT
GATGTGGATATCAGGAAGGATCTTTATGGAAACATTGTGCTTAGTGGTGGCACCACAATGTTCGATGGGATTGGTGAT
AGGATGAGTAAAGAGATCACAGCGTTGGCTCCAAGCAGTATGAAGATCAAAGTGGTGGCTCCACCGGAAAGGAAGTAC
AGTGTCTGGATCGGTGGCTCTATCTTGGCTTCCCTCAGTACTTTCCAGCAGGTAAATTACTTACTATACTTAATACAT
AAAGTCTATTAGTGATTTGATGTATAAAGTGTTACAAAAATGTGTTCCAAATTTGCAGATGTGGATTGCGAAAGCGGA
GTATGATGAATCTGGACCGTCAATCGTCCACAGGAAGTGCTTCTGATCAAAAGTCACCAAGTAAAACAAGAGCGGTAA
AAATTTTGATATCAGTTTTTCACCCTGAAGCCAGTTGCTATAATTACTCACAACTTCTCTATTTGTGTTCTTTTATTC
TTGTCCCTCGTTGTTCATTTTAATCTCTTTTTTGCAACAAAGCAACTTAAAAAAACAGAGCAGTCATTAACAGAATGT
TATTATTATATATATGTATACATATTAGTATACACCCATTATTTCATTAAAACATTTATCATATAAGGATAGGATTCT
ATACATCGATATATTTATTTTGTTGACACTATTCAGCACATGCTTATGTCTTATCTTGTTAGTATATGTAACCAAAGA
CAAATAATAGATGCTACAAATTGTTTTCTTTGAAGCAAAAATTTCAATCTTAAAATTGTTTTTTTCCAGGTTACACAA
AAAAAACTTGTAGTTTGTAAATTTTCTATACAATTTTGGGGATCTCAACAAGAACATGAACTTCAACTTCTAGTCATA
TGACGACCTGAGTCTGCGCGGCTGTGAATCTCTTTGCTGCAGTAAATGTTTACAAGTGGTGTGTAAATTGGTACTGAT
TCAAAAGCTTTAAGAAATCTACACATTTCGTGAAATTATTTAGCAGACTTGATATTAAAAATCTAGGATAAAATGACT
ATCCAAAGACAAATAGGACTGTTTCACATGTTCCCCTGATTCTTGTAGCTCATAACTCATCAGCAGTTAACTTTTCTA
CCTCATACACGCTCGCAATNCGTTTGGAATTATCAGCTNTAATTTTTCTAATTCTTTGGAAATTATTAGCAGCTCGAT
CAAATGGGGCATGGCTTCTTCTTCTATCTGCAACTCATCTAAACTTTCCATGAAGAAACAAAGCT
```

The sequence below is the same *Arabidopsis* sequence after coding probabilities have been determined without a bias, the coding strand has been determined, and each nucleotide has been classified in its most probable state of the four on the coding strand (dashes represent the state of noncoding).

```
  1: ------------------------------------------------------------1
 61: 1111111111113133333333333333333133333333333333333333333333333
121: 3333233333333333333333333333333133333333333333333333333333333
181: 3333333333333333333333333333333333333133333133333333333333333
241: 3333333331331333333331333333333333333333333333333333333333133
301: 3333333333333331333333333333333333331333333333333333333333333
361: 333-33333-333333-3333333333333333-333333333333333333333333333
421: 333333333333--3--3---333333333-33----------------------------
481: -----------------------------------------------11---11-1-
541: -111111111111111111111111111111111111111111111111111111-111
601: 1111111111111111111111111111111111111111111111111111111-1111
661: 1111111111-111-1111111111111-111111111111111111111111111111
721: 1111111111111-11111-11111111-1111111111111111111111111111111
781: 111111111111111111111111111111111111111111111111111111111111
```

-continued

```
 841: 1111111111111111111111111111111111111111111111111-1111
 901: 1111111111111111-111111111111111111111111111-1111111111
 961: 1111111111111111111111111111111111111111111111111111111
1021: 1111111111111111111111111111111111111111111111111111111
1081: 11111111111113111111111111131------------------------
1141: -------------------------------------------------------
1201: ------222-2222222222-22-222-222222-3333333333333333333333
1261: 3333333333333333--33-3--3--3----33-33333333-333---------
1321: ---333--3-----------------------------------------------
1381: -------------------------------------------------------
1441: -------------------------------------------------------
1501: -------------------------------------------------------
1561: -------------------------------------------------------
1621: -------------------------------------------------------
1681: -------------------------------------------------------
1741: -------------------------------------------------------
1801: -------------------1--1--1-----------------------------
1861: -------------------------------------------------------
1921: -------------------------------------------------------
1981: ----------3---33-3-------333-3-------------------------3
2041: 3-3133-33-33-3----13-22222-222222-2222222222222-2----------2
2101: --22--------2222-1222222222222222221222222222222222222222222
2161: 22222
```

40

The classifications are now filtered. First, simple gaps are filled (XYX are reclassified as XXX):

```
  1: -----------------------------------------------------1
 61: 11111111111131333333333333333313333333333333333333333333
121: 3333233333333333333333333333331333333333333333333333333333
181: 33333333333333333333333333333333333133333133333333333133333
241: 33333333313313333333331333333333333333333333333333333333133
301: 3333333333333331333333333333333331333333333333333333333333
361: 3333333333333333333333333333333333333333333333333333333333
421: 333333333333--3--3---333333333333-------------------------
481: ---------------------------------------------11---1111-
541: -111111111111111111111111111111111111111111111111111111
601: 11111111111111111111111111111111111111111111111111111111
661: 11111111111111111111111111111111111111111111111111111111
721: 11111111111111111111111111111111111111111111111111111111
```

-continued

```
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111131111111111111111131---------------------------
1141: ------------------------------------------------------------
1201: ------2222222222222222222222222222-3333333333333333333333333
1261: 3333333333333333--3333--3--3----333333333333333-------------
1321: ---333--3---------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: --------------------1--1--1---------------------------------
1861: ------------------------------------------------------------
1921: ------------------------------------------------------------
1981: ----------3---3333-------33333-----------------------------3
2041: 33313333333333----13-2222222222222222222222222222----------2
2101: --22--------2222-1222222222222222221222222222222222222222222
2161: 22222
```

Next, XXYXX gaps are reclassified as XXXXX:

```
   1: ----------------------------------------------------------1
  61: 1111111111113133333333333333333333333333333333333333333333333333
 121: 333333333333333333333333333333333333333333333333333333333333
 181: 333333333333333333333333333333333333333333333333333333333333
 241: 333333333333333333333333333333333333333333333333333333333333
 301: 333333333333333333333333333333333333333333333333333333333333
 361: 333333333333333333333333333333333333333333333333333333333333
 421: 333333333333---------333333333333---------------------------
 481: ---------------------------------------------11---1111-
 541: -1111111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
```

```
 781: 111111111111111111111111111111111111111111111111111111111
 841: 111111111111111111111111111111111111111111111111111111111
 901: 111111111111111111111111111111111111111111111111111111111
 961: 111111111111111111111111111111111111111111111111111111111
1021: 111111111111111111111111111111111111111111111111111111111
1081: 1111111111111111111111111131--------------------------
1141: ---------------------------------------------------------
1201: ------222222222222222222222222-3333333333333333333333333
1261: 3333333333333333--3333----------333333333333333-------------
1321: ---333---------------------------------------------------
1381: ---------------------------------------------------------
1441: ---------------------------------------------------------
1501: ---------------------------------------------------------
1561: ---------------------------------------------------------
1621: ---------------------------------------------------------
1681: ---------------------------------------------------------
1741: ---------------------------------------------------------
1801: ---------------------------------------------------------
1861: ---------------------------------------------------------
1921: ---------------------------------------------------------
1981: --------------3333-------33333-------------------------3
2041: 3333333333333----13-2222222222222222222222222----------
2101: --22--------2222-12222222222222222222222222222222222222
2161: 22222
```

Next, XXYYXX gaps are reclassified as XXXXXX:

```
   1: ------------------------------------------------------1
  61: 111111111111313333333333333333333333333333333333333333333
 121: 333333333333333333333333333333333333333333333333333333333
 181: 333333333333333333333333333333333333333333333333333333333
 241: 333333333333333333333333333333333333333333333333333333333
 301: 333333333333333333333333333333333333333333333333333333333
 361: 333333333333333333333333333333333333333333333333333333333
 421: 333333333333---------333333333333-------------------------
 481: -----------------------------------------------------11111
 541: 111111111111111111111111111111111111111111111111111111111
 601: 111111111111111111111111111111111111111111111111111111111
 661: 111111111111111111111111111111111111111111111111111111111
 721: 111111111111111111111111111111111111111111111111111111111
```

-continued

```
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111111111111111111131-----------------------------
1141: ------------------------------------------------------------
1201: ------2222222222222222222222222-3333333333333333333333333333
1261: 3333333333333333333333----------333333333333333-------------
1321: ---333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
1921: ------------------------------------------------------------
1981: --------------3333-------33333----------------------------3
2041: 3333333333333----13-2222222222222222222222222---------------
2101: ------------222222222222222222222222222222222222222222222222
2161: 22222
```

Next, XYYX gaps are reclassified as XXXX:

```
   1: -----------------------------------------------------------1
  61: 11111111111131333333333333333333333333333333333333333333333333
 121: 333333333333333333333333333333333333333333333333333333333333
 181: 333333333333333333333333333333333333333333333333333333333333
 241: 333333333333333333333333333333333333333333333333333333333333
 301: 333333333333333333333333333333333333333333333333333333333333
 361: 333333333333333333333333333333333333333333333333333333333333
 421: 333333333333---------333333333333---------------------------
 481: --------------------------------------------------------11111
 541: 111111111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
```

-continued

```
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 11111111111111111111111111111131----------------------------
1141: ------------------------------------------------------------
1201: ------2222222222222222222222222-3333333333333333333333333333
1261: 333333333333333333333333----------333333333333333-----------
1321: ---333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
1921: ------------------------------------------------------------
1981: --------------3333-------33333-----------------------------3
2041: 3333333333333----13-22222222222222222222222222----------
2101: --------------2222222222222222222222222222222222222222222222
2161: 22222
```

Next, XYX gaps are reclassified as XXX:

```
  1: -----------------------------------------------------------1
 61: 1111111111111133333333333333333333333333333333333333333333333
121: 333333333333333333333333333333333333333333333333333333333333
181: 333333333333333333333333333333333333333333333333333333333333
241: 333333333333333333333333333333333333333333333333333333333333
301: 333333333333333333333333333333333333333333333333333333333333
361: 333333333333333333333333333333333333333333333333333333333333
421: 333333333333---------333333333333------------------------
481: -----------------------------------------------------11111
541: 111111111111111111111111111111111111111111111111111111111111
601: 111111111111111111111111111111111111111111111111111111111111
661: 111111111111111111111111111111111111111111111111111111111111
721: 111111111111111111111111111111111111111111111111111111111111
```

-continued

```
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 111111111111111111111111111111111----------------------------
1141: ------------------------------------------------------------
1201: ------2222222222222222222222222-3333333333333333333333333333
1261: 333333333333333333333333----------333333333333333-----------
1321: ---333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
1921: ------------------------------------------------------------
1981: --------------3333-------33333-----------------------------3
2041: 3333333333333----13-2222222222222222222222222222-----------
2101: ------------22222222222222222222222222222222222222222222222
2161: 22222
```

Next, regions between coding regions that are not introns are reclassified according to the adjacent sequences:

```
  1: -----------------------------------------------------------1
 61: 1111111111111333333333333333333333333333333333333333333333
121: 333333333333333333333333333333333333333333333333333333333333
181: 333333333333333333333333333333333333333333333333333333333333
241: 333333333333333333333333333333333333333333333333333333333333
301: 333333333333333333333333333333333333333333333333333333333333
361: 333333333333333333333333333333333333333333333333333333333333
421: 3333333333333333333333333333333----------------------------
481: -------------------------------------------------------11111
541: 111111111111111111111111111111111111111111111111111111111111
601: 111111111111111111111111111111111111111111111111111111111111
661: 111111111111111111111111111111111111111111111111111111111111
721: 111111111111111111111111111111111111111111111111111111111111
```

-continued

```
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 11111111111111111111111111111-------------------------------
1141: ------------------------------------------------------------
1201: ------222222222222222222222222222233333333333333333333333333
1261: 333333333333333333333333333333333333333333333333333333333333
1321: 333333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
1921: ------------------------------------------------------------
1981: --------------3333333333333333333333333333333333333333333333
2041: 333333333333333311132222222222222222222222222222222222222222
2101: 222222222222222222222222222222222222222222222222222222222222
2161: 22222
```

Next, the sequence is checked for frameshifts and reclassified accordingly:

```
   1: -----------------------------------------------------------1
  61: 111111111111111111111111111111111111111111111111111111111111
 121: 111111111111111111111111111111111111111111111111111111111111
 181: 111111111111111111111111111111111111111111111111111111111111
 241: 111111111111111111111111111111111111111333333333333333333333
 301: 333333333333333333333333333333333333333333333333333333333333
 361: 333333333333333333333333333333333333333333333333333333333333
 421: 3333333333333333333333333333333333--------------------------
 481: -------------------------------------------------------11111
 541: 111111111111111111111111111111111111111111111111111111111111
 601: 111111111111111111111111111111111111111111111111111111111111
 661: 111111111111111111111111111111111111111111111111111111111111
```

-continued
```
 721: 111111111111111111111111111111111111111111111111111111111111
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111111111111111111--------------------------------
1141: ------------------------------------------------------------
1201: ------222222222222222222222222222222222222222233333333333333
1261: 333333333333333333333333333333333333333333333333333333333333
1321: 333333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
1921: ------------------------------------------------------------
1981: --------------3333333333333333333333333333333333333333333333
2041: 333333333333333333333333333333333322222222222222222222222222
2101: 222222222222222222222222222222222222222222222222222222222222
2161: 22222
```

Finally, the sequence is translated according to each class in each coding region, where an "x" indicates a stop codon:

```
  1: XRFFRALxAVLATPVxWLGWDKRMLMLETRLNQNVVSxLxSTQLSMELLIIGMTWRRFGI  (SEQ. ID. NO. 2)

61: TLSTMSFVLPLKNIRXLTEAPLNPKANREKMTQIMFETFNTPAMYVAIQAVLSLYASGRT

121: TGQYITTFFLYRXSGDGVSHTVPIYEGYALPHAILRLDLAGRDLTDHLMKILTERGYSFT

181: TTAEREIVRDMKEKLSYIALDFEQELETSKTSSSVEKSFELPDGQVITIGAERFRCPEVL

241: FQPSMIGMENPGIHETTYNSIMKCDVDIRKDLYGNIVLSGGTTMFDGIGDRMSKEITALA

301: PSSMKIKVVAPPERKYSVWIGGSIXVPNLQMWIAKAEYXNLDRQSSTGSASDQKSPSKTR

361: AVKILXNSSAVNFSTSYTLAIRLELSALIFLISLEIISSSIKWGMASSSICNSSKLSMKK

421: QSX
```

The following sequence is the same *Arabidopsis* sequence used above, but with an applied bias. Two bias functions are given by equations XXXIX and XL:

$$\phi_1(\sigma) = \begin{cases} 0.95 & \text{if } \sigma \in \{1^+, 2^+, 3^+, 1^-, 2^-, 3^-\} \\ 0.05 & \text{if } \sigma = N \end{cases} \quad \text{(XXXIX)}$$

$$\phi_2(\sigma) = \begin{cases} 0.05 & \text{if } \sigma \in \{1^+, 2^+, 3^+, 1^-, 2^-, 3^-\} \\ 0.95 & \text{if } \sigma = N \end{cases} \quad \text{(XL)}$$

where $\phi_1$ is applied to a range of the DNA to which an EST has been associated, while $\phi_2$ is applied to a range of the DNA to which a gap (or intron) in the EST has been associated. Specifically, $\phi_1$ is applied to nucleotides 1093 through 1137 and 1219 through 1291, while $\phi_2$ is applied to nucleotides 1138 through 1218. The probabilities are calculated with the bias, the coding strand is determined, and each nucleotide is classified as the most likely state. The resulting sequence is depicted below.

```
   1: ------------------------------------------------------------1
  61: 111111111111131333333333333333331333333333333333333333333333
 121: 333323333333333333333333333333331333333333333333333333333333
 181: 333333333333333333333333333333333333331333331333333333333133333
 241: 333333333133133333333313333333333333333333333333333333333133
 301: 333333333333333313333333333333333333331333333333333333333333
 361: 333-33333-333333-3333333333333333-333333333333333333333333
 421: 333333333333--3--3---333333333-33--------------------------
 481: --------------------------------------------------11---11-1-
 541: -111111111111111111111111111111111111111111111111111111-111
 601: 1111111111111111111111111111111111111111111111111111111-1111
 661: 1111111111-111-1111111111111-111111111111111111111111111111
 721: 111111111111-11111-11111111-111111111111111111111111111111
 781: 111111111111111111111111111111111111111111111111111111111111
 841: 1111111111111111111111111111111111111111111111111111111-1111
 901: 1111111111111111-11111111111111111111111111-1111111111111
 961: 111111111111111111111111111111111111111111111111111111111111
1021: 111111111111111111111111111111111111111111111111111111111111
1081: 111111111111131111111111111131111111-1--------------------
1141: ------------------------------------------------------------
1201: ------------------221221222122222213333333333333333333333333
1261: 333333333333333333333333333333-33-33333333-333-------------
1321: ---333--3---------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: --------------------1--1---1--------------------------------
1861: ------------------------------------------------------------
```

```
                      -continued
1921: ------------------------------------------------------------

1981: ----------3---33-3-------333-3-----------------------------3

2041: 3-3133-33-33-3----13-22222-222222-2222222222222-2----------2

2101: --22--------2222-1222222222222222221222222222222222222222222

2161: 22222
```

Filtering steps are then applied as before: XYX to XXX:

```
   1: ------------------------------------------------------------1

61: 111111111111131333333333333333333133333333333333333333333333

121: 333323333333333333333333333333331333333333333333333333333333

181: 333333333333333333333333333333333333331333331333333333133333

241: 333333333133133333333313333333333333333333333333333333333133

301: 333333333333333133333333333333333333133333333333333333333333

361: 333333333333333333333333333333333333333333333333333333333333

421: 333333333333--3--3---333333333333-------------------------

481: -----------------------------------------------11---1111-

541: -11111111111111111111111111111111111111111111111111111111111

601: 111111111111111111111111111111111111111111111111111111111111

661: 111111111111111111111111111111111111111111111111111111111111

721: 111111111111111111111111111111111111111111111111111111111111

781: 111111111111111111111111111111111111111111111111111111111111

841: 111111111111111111111111111111111111111111111111111111111111

901: 111111111111111111111111111111111111111111111111111111111111

961: 111111111111111111111111111111111111111111111111111111111111

1021: 111111111111111111111111111111111111111111111111111111111111

1081: 11111111111113111111111111111311111111111-------------------

1141: ------------------------------------------------------------

1201: -----------------221221222122222213333333333333333333333333

1261: 333333333333333333333333333333333333333333333------------

1321: ---333--3---------------------------------------------------

1381: ------------------------------------------------------------

1441: ------------------------------------------------------------

1501: ------------------------------------------------------------

1561: ------------------------------------------------------------

1621: ------------------------------------------------------------

1681: ------------------------------------------------------------

1741: ------------------------------------------------------------

1801: --------------------1--1--1---------------------------------

1861: ------------------------------------------------------------
```

-continued

```
1921: ------------------------------------------------------------
1981: ----------3---3333-------33333----------------------------3
2041: 33313333333333-----13-2222222222222222222222222222----------2
2101: --22--------2222-122222222222222222212222222222222222222222
2161: 22222
```

XXYXX to XXXXX:

```
   1: ------------------------------------------------------------1
  61: 11111111111131333333333333333333333333333333333333333333333
 121: 333333333333333333333333333333333333333333333333333333333333
 181: 333333333333333333333333333333333333333333333333333333333333
 241: 333333333333333333333333333333333333333333333333333333333333
 301: 333333333333333333333333333333333333333333333333333333333333
 361: 333333333333333333333333333333333333333333333333333333333333
 421: 333333333333---------333333333333-------------------------
 481: --------------------------------------------11---1111-
 541: -11111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 11111111111111111111111111111111111-------------------
1141: ------------------------------------------------------------
1201: ----------------2222222222222222213333333333333333333333
1261: 3333333333333333333333333333333333333333333-------------
1321: ---333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
```

-continued

```
1921: ------------------------------------------------------------
1981: --------------3333-------33333----------------------------3
2041: 3333333333333333----13-2222222222222222222222222222-----------
2101: --22--------2222-1222222222222222222222222222222222222222222
2161: 22222
```

XXYYXX to XXXXXX:

```
   1: -----------------------------------------------------------1
  61: 1111111111113133333333333333333333333333333333333333333333333
 121: 3333333333333333333333333333333333333333333333333333333333333
 181: 3333333333333333333333333333333333333333333333333333333333333
 241: 3333333333333333333333333333333333333333333333333333333333333
 301: 3333333333333333333333333333333333333333333333333333333333333
 361: 3333333333333333333333333333333333333333333333333333333333333
 421: 333333333333---------333333333333-------------------------
 481: --------------------------------------------------------11111
 541: 111111111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111111111111111111111111111111-------------------
1141: ------------------------------------------------------------
1201: -----------------2222222222222222213333333333333333333333333
1261: 33333333333333333333333333333333333333333333--------------
1321: ---333-----------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
```

-continued

```
1921: ------------------------------------------------------------
1981: --------------3333-------33333---------------------------3
2041: 33333333333333----13-2222222222222222222222222222-----------
2101: -----------2222222222222222222222222222222222222222222222
2161: 22222
```

XYYX to XXXX:

```
   1: ------------------------------------------------------------1
  61: 11111111111131333333333333333333333333333333333333333333333333
 121: 333333333333333333333333333333333333333333333333333333333333
 181: 333333333333333333333333333333333333333333333333333333333333
 241: 333333333333333333333333333333333333333333333333333333333333
 301: 333333333333333333333333333333333333333333333333333333333333
 361: 333333333333333333333333333333333333333333333333333333333333
 421: 33333333333---------333333333333-------------------------
 481: -------------------------------------------------------11111
 541: 111111111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111111111111111111111111111111--------------------
1141: ------------------------------------------------------------
1201: ----------------2222222222222222213333333333333333333333333
1261: 3333333333333333333333333333333333333333333------------
1321: ---333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
```

-continued

```
1921: ------------------------------------------------------------
1981: --------------3333-------33333----------------------------3
2041: 33333333333333-----13-2222222222222222222222222222-----------
2101: -------------
      2222222222222222222222222222222222222222222222222
2161: 22222
```

XYX to XXX:

```
   1: ------------------------------------------------------------1
  61: 11111111111113333333333333333333333333333333333333333333333333
 121: 333333333333333333333333333333333333333333333333333333333333
 181: 333333333333333333333333333333333333333333333333333333333333
 241: 333333333333333333333333333333333333333333333333333333333333
 301: 333333333333333333333333333333333333333333333333333333333333
 361: 333333333333333333333333333333333333333333333333333333333333
 421: 333333333333---------333333333333--------------------------
 481: -------------------------------------------------------11111
 541: 111111111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111111111111111111111111111111--------------------
1141: ------------------------------------------------------------
1201: ------------------2222222222222222221333333333333333333333333
1261: 3333333333333333333333333333333333333333333-----------------
1321: ---333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
1861: ------------------------------------------------------------
```

```
                         -continued
1921: ------------------------------------------------------------

1981: --------------3333-------3333----------------------------3

2041: 33333333333333----13-2222222222222222222222222222----------

2101: -----------2222222222222222222222222222222222222222222222

2161: 22222
```

Gaps between coding regions that are not introns are filled as before:

```
   1: -----------------------------------------------------------1

61: 111111111111113333333333333333333333333333333333333333333333

121: 333333333333333333333333333333333333333333333333333333333333

181: 333333333333333333333333333333333333333333333333333333333333

241: 333333333333333333333333333333333333333333333333333333333333

301: 333333333333333333333333333333333333333333333333333333333333

361: 333333333333333333333333333333333333333333333333333333333333

421: 3333333333333333333333333333333333-------------------------

481: -------------------------------------------------------11111

541: 111111111111111111111111111111111111111111111111111111111111

601: 111111111111111111111111111111111111111111111111111111111111

661: 111111111111111111111111111111111111111111111111111111111111

721: 111111111111111111111111111111111111111111111111111111111111

781: 111111111111111111111111111111111111111111111111111111111111

841: 111111111111111111111111111111111111111111111111111111111111

901: 111111111111111111111111111111111111111111111111111111111111

961: 111111111111111111111111111111111111111111111111111111111111

1021: 111111111111111111111111111111111111111111111111111111111111

1081: 1111111111111111111111111111111111111111--------------------

1141: ------------------------------------------------------------

1201: ------------------22222222222222222213333333333333333333333

1261: 333333333333333333333333333333333333333333333333333333333333

1321: 333333------------------------------------------------------

1381: ------------------------------------------------------------

1441: ------------------------------------------------------------

1501: ------------------------------------------------------------

1561: ------------------------------------------------------------

1621: ------------------------------------------------------------

1681: ------------------------------------------------------------

1741: ------------------------------------------------------------

1801: ------------------------------------------------------------
```

-continued

```
1861: ------------------------------------------------------------
1921: ------------------------------------------------------------
1981: --------------33333333333333333333333333333333333333333333
2041: 3333333333333333111322222222222222222222222222222222222222
2101: 2222222222222222222222222222222222222222222222222222222222
2161: 22222
```

Frameshifts are verified and nucleotides are reclassified accordingly:

```
   1: -----------------------------------------------------------1
  61: 111111111111111111111111111111111111111111111111111111111111
 121: 111111111111111111111111111111111111111111111111111111111111
 181: 111111111111111111111111111111111111111111111111111111111111
 241: 1111111111111111111111111111111111111111111133333333333333
 301: 333333333333333333333333333333333333333333333333333333333333
 361: 333333333333333333333333333333333333333333333333333333333333
 421: 3333333333333333333333333333333333-------------------------
 481: -------------------------------------------------------11111
 541: 111111111111111111111111111111111111111111111111111111111111
 601: 111111111111111111111111111111111111111111111111111111111111
 661: 111111111111111111111111111111111111111111111111111111111111
 721: 111111111111111111111111111111111111111111111111111111111111
 781: 111111111111111111111111111111111111111111111111111111111111
 841: 111111111111111111111111111111111111111111111111111111111111
 901: 111111111111111111111111111111111111111111111111111111111111
 961: 111111111111111111111111111111111111111111111111111111111111
1021: 111111111111111111111111111111111111111111111111111111111111
1081: 1111111111111111111111111111111111111-----------------------
1141: ------------------------------------------------------------
1201: -----------------22222222222222222222222222222233333333333333
1261: 333333333333333333333333333333333333333333333333333333333333
1321: 333333------------------------------------------------------
1381: ------------------------------------------------------------
1441: ------------------------------------------------------------
1501: ------------------------------------------------------------
1561: ------------------------------------------------------------
1621: ------------------------------------------------------------
1681: ------------------------------------------------------------
1741: ------------------------------------------------------------
1801: ------------------------------------------------------------
```

-continued

```
1861: ------------------------------------------------------------
1921: ------------------------------------------------------------
1981: --------------3333333333333333333333333333333333333333333333
2041: 333333333333333333333333333333333332222222222222222222222222
2101: 222222222222222222222222222222222222222222222222222222222222
2161: 22222
```

And the sequence is translated as before:

```
  1: XRFFRALxAVLATPVxWLGWDKRMLMLETRLNQNVVSxLxSTQLSMELLIIGMTWRRFGI  (SEQ. ID. NO.3)
 61: TLSTMSFVLPLKNIRXLTEAPLNPKANREKMTQIMFETFNTPAMYVAIQAVLSLYASGRT
121: TGQYITTFFLYRXSGDGVSHTVPIYEGYALPHAILRLDLAGRDLTDHLMKILTERGYSFT
181: TTAEREIVRDMKEKLSYIALDFEQELETSKTSSSVEKSFELPDGQVITIGAERFRCPEVL
241: FQPSMIGMENPGIHETTYNSIMKCDVDIRKDLYGNIVLSGGTTMFDGIGDRMSKEITALA
301: PSSMKIKVVAPPERKYSVWIGGSILASXQMWIAKAEYXNLDRQSSTGSASDQKSPSKTRA
361: VKILXNSSAVNFSTSYTLAIRLELSALIFLISLEIISSSIKWGMASSSICNSSKLSMKKQ
421: SX
```

The resulting amino acid sequence (SEQ. ID. NO. 3) differs from the amino acid sequence calculated without a bias (SEQ. ID. NO. 2). The relative accuracy of the two amino acid sequences can be determined by comparison to a known sequence. SEQ. ID. NO. 2 and SEQ. ID. NO. 3 are compared to the translation of the actin gene from *Arabidopsis thaliana, columbia* (SEQ. ID. NO. 4). Dashes indicate gaps in the sequence and asterisks indicate a match among all three sequences. The predicted amino acid sequences (SEQ. ID. NOs. 2 and 3) are based on an *Arabidopsis thaliana, landsberg* ecotype. A comparison of the predicted with a known *Arabidopsis thaliana, columbia* ecotype amino acid sequence (SEQ. ID. NO. 4) is shown below. The sequence set forth in Box A illustrates an area of the biased sequence that shows a higher level of identity with the *Arabidopsis thaliana, columbia* sequence.

```
unbiased   -XRFFRALX-AVLATPVXWLGWDKRMLMLETRLNQNVVSX--LXSTQLSMELLIIG---M
biased     -XRFFRALX-AVLATPVXWLGWDKRMLMLETRLNQNVVSX--LXSTQLSMELLIIG---M
columbia   GDDAPRAVFPSIVGRPR-HTGVMVGMGQKDAYVGDEAQSKRGILTLKYPIEHGIVNNWDD
            **         *    *   *        *       * * unbiased   TWRRFGITLSTMSFVLPLKNIRXLTEAPLNPKANREKMTQIMFETFNTPAMYVAIQAVLS
biased     TWRRFGITLSTMSFVLPLKNIRXLTEAPLNPKANREKMTQIMFETFNTPAMYVAIQAVLS
columbia   MEKIWHHTFYNELRVAPEEHPVLLTEAPLNPKANREKMTQIMFETFNTPAMYVAIQAVLS
             *  *      ********************************* unbiased   LYASGRTTGQYTTTFFLYRXSGDGVSHTVPIYEGYALPHAILRLDLAGRDLTDHLMKTLT
biased     LYASGRTTGQYITTFFLYRXSGDGVSHTVPIYEGYAIPHAILRLDLAGRDLTDHLMKILT
columbia   L-ASGRTTGG------IVLDSGDGVSHTVPIYEGYALPHAILRLDLAGRDLTDHLMKILT
           * *****        ***************************** unbiased   ERGYSFTTTAEREIVRDMKEKLSYIALDFEQELETSKTSSSVEKSFELPDGQVITIGAER
biased     ERGYSFTTTAEREIVRDMKEKLSYIALDFEQELETSKTSSSVEKSFELPDGQVITIGAER
columbia   ERGYSFTTTAEREIVRDMKEKLSYIAIDFEQELETSKTSSSVEKSEELPDGQVITIGAER
           ***********************  ************  *********** unbiased   FRCPEVLFQPSMIGMENPGIHETTYNSIMKCDVDIRKDLYGNIVLSGGTTMFDGIGDRMS
biased     FRCPEVLFQPSMIGMENPGIHETTYNSIMKCDVDTRKDLYGNTVLSGGTTMFDGIGDRMS
columbia   FRCPEVLFQPSMIGMENPGIHETTYNSIMKCDVDIRKDLYGNIVLSGGTTMFGGIGDRMS
           **********************************   *******  ***** ******

Box A
unbiased   KEITALAPSSMKIKVVAPPERKYSV|WIGGSIX----|VPNLQMWIAKAEYXNLDRQSSTG
biased     KEITALAPSSMKIKVVAPPERKYSV|WIGGSILAS---|-XQMWIAKAEYXNLDRQSSTG
columbia   KEITALAPSSMKIKVVAPPERKYSV|WIGGSILASL|STFQQMQMWIAKAEY------DESG
           ************************ ******         ***********      *
```

```
unbiased    SASDQKSPSKTRAVKILXNSSAVNFSTSYTLAIRLELSALIFLISLEIISSSIKWGMASS
biased      SASDQKSPSKTRAVKILXNSSAVNFSTSYTLAIRLELSALIFLISLEIISSSIKWGMASS
columbia    -------PS------IVHRKCF--------------------------------------
                   **      * unbiased    SICNSSKLSMKKQSX (SEQ ID NO: 2)
biased      SICNSSKLSMKKQSX (SEQ ID NO: 3)
columbia    -------------- (SEQ ID NO: 4)
```

I claim:

1. A method for determining coding features within a nucleic acid sequence by determining a probability for each of one or more states for more than one examined nucleotide in said nucleic acid sequence, comprising:
   a) determining an initial oligonucleotide probability for each of said states for an initial oligonucleotide in a window of a first examined nucleotide;
   b) determining transition probabilities for each of said states for nucleotides within said window following said initial oligonucleotide;
   c) using said initial oligonucleotide probability and said transition probabilities to determine a plurality of window probabilities, wherein said plurality comprises a window probability corresponding to each of said states for said examined nucleotide;
   d) applying a bias function to said plurality of window probabilities, to determine a probability for each of said states for said examined nucleotide, wherein a value being used in said bias function is different in at least one state from the other states for said examined nucleotide;
   e) repeating steps a) through d) for each remaining examined nucleotide in said nucleic acid sequence,
   wherein said more than one examined nucleotide are contiguous, and step e) is performed sequentially from said first examined nucleotide to a last examined nucleotide,
   wherein said probability for each of said states for said more than one examined nucleotide is determined using an inhomogeneous Markov model having eight states, wherein said eight states are: first reading frame positive strand (1+); second reading frame positive strand (2+); third reading frame positive strand (3+); first reading frame negative strand (1−); second reading frame negative strand (2−); third reading frame negative strand (3−); noncoding positive strand (N+); and noncoding negative strand (N−),
   wherein said probability for each of said states for said more than one examined nucleotide is determined using the equation $$P'(\sigma \mid S) = \frac{\phi(\sigma) \cdot P(\sigma) \cdot P(S \mid \sigma)}{\sum_i [\phi(i) \cdot P(i) \cdot P(S \mid i)]},$$

wherein i and σ are each one of said eight states,
wherein $P'(\sigma|S)$ is the probability of said inhomogeneous Markov model being in state σ after having examined nucleic acid sequence S,
wherein $P(S|\sigma)$ is the probability of said inhomogeneous Markov model generating sequence S while in state σ,
wherein $P(S|i)$ is the probability of said inhomogeneous Markov model generating sequence S while in state i,
wherein $P(i)$ is a probability of said inhomogeneous Markov model being in state i, before having examined any sequence,
wherein $P(\sigma)$ is the probability of said inhomogeneous Markov model being in state σ, before having examined any sequence,
wherein $\phi(\sigma)$ is the bias function corresponding to said state σ, and
wherein $\phi(i)$ is the bias function corresponding to said state i; and
   f) outputting said nucleic acid sequence as most probable states of said probability states for each of said states for each of more than one examined nucleotide wherein said most probable states demarcate said coding features of said nucleic acid sequence and outputting said coding features as a translated protein sequence.

2. The method of claim 1, wherein said nucleic acid sequence is part of a longer nucleic acid sequence.

3. The method of claim 1, wherein said examined nucleotide in said more than one examined nucleotide is the middle nucleotide in its own window.

4. The method of claim 1, wherein the value being used in said bias function is between 0.0 and 0.9, or greater than 1.1, in one or more of said states for said examined nucleotide.

* * * * *